US012751821B2

(12) United States Patent
O'Brien et al.

(10) Patent No.: US 12,751,821 B2
(45) Date of Patent: Oct. 6, 2026

(54) REPLACEMENT HEART VALVE SYSTEM

(71) Applicant: BOSTON SCIENTIFIC SCIMED, INC., Maple Grove, MN (US)

(72) Inventors: Gavin O'Brien, Dublin (IE); Tim O'Connor, Galway (IE); Chris Cullen, Galway (IE); Jingwen Ping, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 370 days.

(21) Appl. No.: 18/597,832

(22) Filed: Mar. 6, 2024

(65) Prior Publication Data

US 2024/0299162 A1 Sep. 12, 2024

Related U.S. Application Data

(60) Provisional application No. 63/451,255, filed on Mar. 10, 2023.

(51) Int. Cl.
*A61F 2/24* (2006.01)
*A61M 25/10* (2013.01)

(52) U.S. Cl.
CPC .......... *A61F 2/2418* (2013.01); *A61F 2/2433* (2013.01); *A61F 2/2436* (2013.01); *A61F 2250/0048* (2013.01); *A61M 25/1002* (2013.01)

(58) Field of Classification Search
CPC .... A61F 2/2418; A61F 2/2436; A61F 2/2433; A61F 2250/0048; A61M 25/1002
See application file for complete search history.

(56) References Cited

U.S. PATENT DOCUMENTS 1,519,200 A 12/1924 Griffith
2,682,057 A 6/1954 Lord
(Continued)

FOREIGN PATENT DOCUMENTS

AU 2002329324 B2 7/2007
CN 1338951 A 3/2002
(Continued)

OTHER PUBLICATIONS

US 8,062,356 B2, 11/2011, Salahieh et al. (withdrawn)
(Continued)

*Primary Examiner* — Javier G Blanco
(74) *Attorney, Agent, or Firm* — Seager, Tufte & Wickhem LLP

(57) ABSTRACT

A replacement heart valve system may include a replacement heart valve implant including an expandable framework configured to shift from a radially collapsed to a radially expanded configuration, wherein the framework is self-biased toward the radially expanded configuration, and a plurality of valve leaflets attached to the framework. The replacement heart valve system may include an implant delivery system including a handle and an elongate shaft assembly including a tubular member fixedly attached to the handle, and an implant holding portion configured to constrain the framework in the radially collapsed configuration. The elongate shaft assembly includes an expandable balloon disposed on the tubular member within the implant holding portion, the balloon being configured to shift between deflated and inflated configurations. When the framework is constrained within the implant holding portion, at least a portion of the framework extends distal of the balloon in the deflated configuration.

5 Claims, 6 Drawing Sheets

(56) References Cited

U.S. PATENT DOCUMENTS

| | | | |
|---|---|---|---|
| 2,701,559 | A | 2/1955 | Cooper |
| 2,832,078 | A | 4/1958 | Williams |
| 3,029,819 | A | 4/1962 | Starks |
| 3,099,016 | A | 7/1963 | Lowell |
| 3,113,586 | A | 12/1963 | Edmark |
| 3,130,418 | A | 4/1964 | Head et al. |
| 3,143,742 | A | 8/1964 | Cromie |
| 3,221,006 | A | 11/1965 | Moore et al. |
| 3,334,629 | A | 8/1967 | Cohn |
| 3,365,728 | A | 1/1968 | Edwards et al. |
| 3,367,364 | A | 2/1968 | Cruz et al. |
| 3,409,013 | A | 11/1968 | Henry |
| 3,445,916 | A | 5/1969 | Schulte |
| 3,540,431 | A | 11/1970 | Mobin-Uddin |
| 3,548,417 | A | 12/1970 | Kischer et al. |
| 3,570,014 | A | 3/1971 | Hancock |
| 3,587,115 | A | 6/1971 | Shiley |
| 3,592,184 | A | 7/1971 | Watkins et al. |
| 3,628,535 | A | 12/1971 | Ostrowsky et al. |
| 3,642,004 | A | 2/1972 | Osthagen et al. |
| 3,657,744 | A | 4/1972 | Ersek |
| 3,671,979 | A | 6/1972 | Moulopoulos |
| 3,714,671 | A | 2/1973 | Goodenough et al. |
| 3,725,961 | A | 4/1973 | Magovern et al. |
| 3,755,823 | A | 9/1973 | Hancock |
| 3,795,246 | A | 3/1974 | Sturgeon |
| 3,839,741 | A | 10/1974 | Haller |
| 3,868,956 | A | 3/1975 | Alfidi et al. |
| 3,874,388 | A | 4/1975 | King et al. |
| 3,983,581 | A | 10/1976 | Angell et al. |
| 3,997,923 | A | 12/1976 | Possis |
| 4,035,849 | A | 7/1977 | Angell et al. |
| 4,056,854 | A | 11/1977 | Boretos et al. |
| 4,084,268 | A | 4/1978 | Ionescu et al. |
| 4,106,129 | A | 8/1978 | Carpentier et al. |
| 4,222,126 | A | 9/1980 | Boretos et al. |
| 4,233,690 | A | 11/1980 | Akins |
| 4,265,694 | A | 5/1981 | Boretos et al. |
| 4,291,420 | A | 9/1981 | Reul |
| 4,297,749 | A | 11/1981 | Davis et al. |
| 4,323,358 | A | 4/1982 | Lentz et al. |
| 4,326,306 | A | 4/1982 | Poler |
| 4,339,831 | A | 7/1982 | Johnson |
| 4,343,048 | A | 8/1982 | Ross et al. |
| 4,345,340 | A | 8/1982 | Rosen |
| 4,373,216 | A | 2/1983 | Klawitter |
| 4,406,022 | A | 9/1983 | Roy |
| 4,423,809 | A | 1/1984 | Mazzocco |
| 4,425,908 | A | 1/1984 | Simon |
| 4,470,157 | A | 9/1984 | Love |
| 4,484,579 | A | 11/1984 | Meno et al. |
| 4,501,030 | A | 2/1985 | Lane |
| 4,531,943 | A | 7/1985 | Tassel et al. |
| 4,535,483 | A | 8/1985 | Klawitter et al. |
| 4,574,803 | A | 3/1986 | Storz |
| 4,580,568 | A | 4/1986 | Gianturco |
| 4,592,340 | A | 6/1986 | Boyles |
| 4,602,911 | A | 7/1986 | Ahmadi et al. |
| 4,605,407 | A | 8/1986 | Black et al. |
| 4,610,688 | A | 9/1986 | Silvestrini et al. |
| 4,612,011 | A | 9/1986 | Kautzky |
| 4,617,932 | A | 10/1986 | Kornberg |
| 4,643,732 | A | 2/1987 | Pietsch et al. |
| 4,647,283 | A | 3/1987 | Carpentier et al. |
| 4,648,881 | A | 3/1987 | Carpentier et al. |
| 4,655,218 | A | 4/1987 | Kulik et al. |
| 4,655,771 | A | 4/1987 | Wallsten et al. |
| 4,662,885 | A | 5/1987 | DiPisa |
| 4,665,906 | A | 5/1987 | Jervis |
| 4,680,031 | A | 7/1987 | Alonso |
| 4,692,164 | A | 9/1987 | Dzemeshkevich et al. |
| 4,705,516 | A | 11/1987 | Barone et al. |
| 4,710,192 | A | 12/1987 | Liotta et al. |
| 4,733,665 | A | 3/1988 | Palmaz et al. |
| 4,755,181 | A | 7/1988 | Igoe |
| 4,759,758 | A | 7/1988 | Gabbay |
| 4,777,951 | A | 10/1988 | Cribier et al. |
| 4,787,899 | A | 11/1988 | Lazarus |
| 4,787,901 | A | 11/1988 | Baykut |
| 4,796,629 | A | 1/1989 | Grayzel |
| 4,819,751 | A | 4/1989 | Shimada et al. |
| 4,829,990 | A | 5/1989 | Thuroff et al. |
| 4,834,755 | A | 5/1989 | Silvestrini et al. |
| 4,851,001 | A | 7/1989 | Taheri |
| 4,856,516 | A | 8/1989 | Hillstead |
| 4,865,600 | A | 9/1989 | Carpentier et al. |
| 4,872,874 | A | 10/1989 | Taheri |
| 4,873,978 | A | 10/1989 | Ginsburg |
| 4,878,495 | A | 11/1989 | Grayzel |
| 4,878,906 | A | 11/1989 | Lindemann et al. |
| 4,883,458 | A | 11/1989 | Shiber |
| 4,885,005 | A | 12/1989 | Nashef et al. |
| 4,909,252 | A | 3/1990 | Goldberger |
| 4,917,102 | A | 4/1990 | Miller et al. |
| 4,922,905 | A | 5/1990 | Strecker |
| 4,927,426 | A | 5/1990 | Dretler |
| 4,954,126 | A | 9/1990 | Wallsten |
| 4,966,604 | A | 10/1990 | Reiss |
| 4,969,890 | A | 11/1990 | Sugita et al. |
| 4,979,939 | A | 12/1990 | Shiber |
| 4,986,830 | A | 1/1991 | Owens et al. |
| 4,994,077 | A | 2/1991 | Dobben |
| 5,002,556 | A | 3/1991 | Ishida et al. |
| 5,002,559 | A | 3/1991 | Tower |
| 5,007,896 | A | 4/1991 | Shiber |
| 5,026,366 | A | 6/1991 | Leckrone |
| 5,032,128 | A | 7/1991 | Alonso |
| 5,037,434 | A | 8/1991 | Lane |
| 5,047,041 | A | 9/1991 | Samuels |
| 5,064,435 | A | 11/1991 | Porter |
| 5,080,668 | A | 1/1992 | Bolz et al. |
| 5,085,635 | A | 2/1992 | Cragg |
| 5,089,015 | A | 2/1992 | Ross |
| 5,122,154 | A | 6/1992 | Rhodes |
| 5,132,473 | A | 7/1992 | Furutaka et al. |
| 5,141,494 | A | 8/1992 | Danforth et al. |
| 5,152,771 | A | 10/1992 | Sabbaghian et al. |
| 5,159,937 | A | 11/1992 | Tremulis |
| 5,161,547 | A | 11/1992 | Tower |
| 5,163,953 | A | 11/1992 | Vince |
| 5,167,628 | A | 12/1992 | Boyles |
| 5,209,741 | A | 5/1993 | Spaeth |
| 5,215,541 | A | 6/1993 | Nashef et al. |
| 5,217,481 | A | 6/1993 | Barbara |
| 5,217,483 | A | 6/1993 | Tower |
| 5,238,004 | A | 8/1993 | Sahatjian et al. |
| 5,258,023 | A | 11/1993 | Reger |
| 5,258,042 | A | 11/1993 | Mehta |
| 5,282,847 | A | 2/1994 | Trescony et al. |
| 5,295,958 | A | 3/1994 | Shturman |
| 5,332,402 | A | 7/1994 | Teitelbaum |
| 5,336,258 | A | 8/1994 | Quintero et al. |
| 5,350,398 | A | 9/1994 | Pavcnik et al. |
| 5,360,444 | A | 11/1994 | Kusuhara |
| 5,370,685 | A | 12/1994 | Stevens |
| 5,389,106 | A | 2/1995 | Tower |
| 5,397,351 | A | 3/1995 | Pavcnik et al. |
| 5,409,019 | A | 4/1995 | Wilk |
| 5,411,552 | A | 5/1995 | Andersen et al. |
| 5,425,739 | A | 6/1995 | Jessen |
| 5,425,762 | A | 6/1995 | Muller |
| 5,431,676 | A | 7/1995 | Dubrul et al. |
| 5,443,446 | A | 8/1995 | Shturman |
| 5,443,449 | A | 8/1995 | Buelna |
| 5,443,477 | A | 8/1995 | Marin et al. |
| 5,443,495 | A | 8/1995 | Buscemi et al. |
| 5,443,499 | A | 8/1995 | Schmitt |
| 5,469,868 | A | 11/1995 | Reger |
| 5,476,506 | A | 12/1995 | Lunn |
| 5,476,510 | A | 12/1995 | Eberhardt et al. |
| 5,480,423 | A | 1/1996 | Ravenscroft et al. |
| 5,480,424 | A | 1/1996 | Cox |
| 5,489,297 | A | 2/1996 | Duran |
| 5,500,014 | A | 3/1996 | Quijano et al. |

(56) References Cited

U.S. PATENT DOCUMENTS 5,507,767 A 4/1996 Maeda et al.
5,522,881 A 6/1996 Lentz
5,534,007 A 7/1996 Germain et al.
5,545,133 A 8/1996 Burns et al.
5,545,209 A 8/1996 Roberts et al.
5,545,211 A 8/1996 An et al.
5,545,214 A 8/1996 Stevens
5,549,665 A 8/1996 Vesely et al.
5,554,185 A 9/1996 Block et al.
5,571,175 A 11/1996 Vanney et al.
5,571,215 A 11/1996 Sterman et al.
5,573,520 A 11/1996 Schwartz et al.
5,575,818 A 11/1996 Pinchuk
5,591,185 A 1/1997 Kilmer et al.
5,591,195 A 1/1997 Taheri et al.
5,607,464 A 3/1997 Trescony et al.
5,609,626 A 3/1997 Quijano et al.
5,628,784 A 5/1997 Strecker
5,645,559 A 7/1997 Hachtman et al.
5,653,745 A 8/1997 Trescony et al.
5,662,671 A 9/1997 Barbut et al.
5,667,523 A 9/1997 Bynon et al.
5,674,277 A 10/1997 Freitag
5,681,345 A 10/1997 Euteneuer
5,693,083 A 12/1997 Baker et al.
5,693,088 A 12/1997 Lazarus
5,693,310 A 12/1997 Gries et al.
5,695,498 A 12/1997 Tower
5,709,713 A 1/1998 Evans et al.
5,713,951 A 2/1998 Garrison et al.
5,713,953 A 2/1998 Vallana et al.
5,716,370 A 2/1998 Williamson et al.
5,716,417 A 2/1998 Girard et al.
5,720,391 A 2/1998 Dohm et al.
5,725,549 A 3/1998 Lam
5,728,068 A 3/1998 Leone et al.
5,733,325 A 3/1998 Robinson et al.
5,735,842 A 4/1998 Krueger et al.
5,749,890 A 5/1998 Shaknovich
5,755,783 A 5/1998 Stobie et al.
5,756,476 A 5/1998 Epstein et al.
5,769,812 A 6/1998 Stevens et al.
5,769,882 A 6/1998 Fogarty et al.
5,772,609 A 6/1998 Nguyen et al.
5,776,188 A 7/1998 Shepherd et al.
5,782,904 A 7/1998 White et al.
5,800,456 A 9/1998 Maeda et al.
5,800,531 A 9/1998 Cosgrove et al.
5,807,405 A 9/1998 Vanney et al.
5,817,126 A 10/1998 Imran
5,824,037 A 10/1998 Fogarty et al.
5,824,041 A 10/1998 Lenker et al.
5,824,043 A 10/1998 Cottone
5,824,053 A 10/1998 Khosravi et al.
5,824,055 A 10/1998 Spiridigliozzi et al.
5,824,056 A 10/1998 Rosenberg
5,824,064 A 10/1998 Taheri
5,840,081 A 11/1998 Andersen et al.
5,843,158 A 12/1998 Lenker et al.
5,843,161 A 12/1998 Solovay
5,855,597 A 1/1999 Jayaraman
5,855,601 A 1/1999 Bessler et al.
5,855,602 A 1/1999 Angell
5,860,966 A 1/1999 Tower
5,860,996 A 1/1999 Urban et al.
5,861,024 A 1/1999 Rashidi
5,861,028 A 1/1999 Angell
5,868,783 A 2/1999 Tower
5,876,419 A 3/1999 Carpenter et al.
5,876,448 A 3/1999 Thompson et al.
5,885,228 A 3/1999 Rosenman et al.
5,888,201 A 3/1999 Stinson et al.
5,891,191 A 4/1999 Stinson
5,895,399 A 4/1999 Barbut et al.
5,906,619 A 5/1999 Olson et al.
5,907,893 A 6/1999 Zadno-Azizi et al.
5,910,154 A 6/1999 Tsugita et al.
5,911,734 A 6/1999 Tsugita et al.
5,925,063 A 7/1999 Khosravi
5,944,738 A 8/1999 Amplatz et al.
5,954,766 A 9/1999 Zadno-Azizi et al.
5,957,949 A 9/1999 Leonhardt et al.
5,968,070 A 10/1999 Bley et al.
5,984,957 A 11/1999 Laptewicz et al.
5,984,959 A 11/1999 Robertson et al.
5,993,469 A 11/1999 McKenzie et al.
5,997,557 A 12/1999 Barbut et al.
6,010,522 A 1/2000 Barbut et al.
6,015,431 A 1/2000 Thornton et al.
6,022,370 A 2/2000 Tower
6,027,520 A 2/2000 Tsugita et al.
6,027,525 A 2/2000 Suh et al.
6,042,598 A 3/2000 Tsugita et al.
6,042,607 A 3/2000 Williamson et al.
6,051,014 A 4/2000 Jang
6,059,827 A 5/2000 Fenton
6,074,418 A 6/2000 Buchanan et al.
6,093,203 A 7/2000 Uflacker
6,096,074 A 8/2000 Pedros
6,110,198 A 8/2000 Fogarty et al.
6,123,723 A 9/2000 Konya et al.
6,132,473 A 10/2000 Williams et al.
6,139,510 A 10/2000 Palermo
6,142,987 A 11/2000 Tsugita
6,146,366 A 11/2000 Schachar
6,162,245 A 12/2000 Jayaraman
6,165,200 A 12/2000 Tsugita et al.
6,165,209 A 12/2000 Patterson et al.
6,168,579 B1 1/2001 Tsugita
6,168,614 B1 1/2001 Andersen et al.
6,171,327 B1 1/2001 Daniel et al.
6,171,335 B1 1/2001 Wheatley et al.
6,179,859 B1 1/2001 Bates et al.
6,187,016 B1 2/2001 Hedges et al.
6,197,053 B1 3/2001 Cosgrove et al.
6,200,336 B1 3/2001 Pavcnik et al.
6,206,911 B1 3/2001 Milo
6,214,036 B1 4/2001 Letendre et al.
6,221,006 B1 4/2001 Dubrul et al.
6,221,091 B1 4/2001 Khosravi
6,221,096 B1 4/2001 Aiba et al.
6,221,100 B1 4/2001 Strecker
6,231,544 B1 5/2001 Tsugita et al.
6,231,551 B1 5/2001 Barbut
6,241,757 B1 6/2001 An et al.
6,245,102 B1 6/2001 Jayaraman
6,251,135 B1 6/2001 Stinson et al.
6,258,114 B1 7/2001 Konya et al.
6,258,115 B1 7/2001 Dubrul
6,258,120 B1 7/2001 McKenzie et al.
6,258,129 B1 7/2001 Dybdal et al.
6,267,783 B1 7/2001 Letendre et al.
6,270,513 B1 8/2001 Tsugita et al.
6,277,555 B1 8/2001 Duran et al.
6,299,637 B1 10/2001 Shaolian et al.
6,302,906 B1 10/2001 Goicoechea et al.
6,306,164 B1 10/2001 Kujawski
6,309,417 B1 10/2001 Spence et al.
6,312,465 B1 11/2001 Griffin et al.
6,319,281 B1 11/2001 Patel
6,327,772 B1 12/2001 Zadno-Azizi et al.
6,336,934 B1 1/2002 Gilson et al.
6,336,937 B1 1/2002 Vonesh et al.
6,338,735 B1 1/2002 Stevens
6,346,116 B1 2/2002 Brooks et al.
6,348,063 B1 2/2002 Yassour et al.
6,352,554 B2 3/2002 Paulis
6,352,708 B1 3/2002 Duran et al.
6,361,545 B1 3/2002 Macoviak et al.
6,363,938 B2 4/2002 Saadat et al.
6,364,895 B1 4/2002 Greenhalgh
6,371,970 B1 4/2002 Khosravi et al.
6,371,983 B1 4/2002 Lane
6,379,383 B1 4/2002 Palmaz et al.

(56) References Cited

U.S. PATENT DOCUMENTS

| | | | |
|---|---|---|---|
| 6,387,122 | B1 | 5/2002 | Cragg |
| 6,398,807 | B1 | 6/2002 | Chouinard et al. |
| 6,402,736 | B1 | 6/2002 | Brown et al. |
| 6,409,750 | B1 | 6/2002 | Hyodoh et al. |
| 6,416,510 | B1 | 7/2002 | Altman et al. |
| 6,425,916 | B1 | 7/2002 | Garrison et al. |
| 6,440,164 | B1 | 8/2002 | DiMatteo et al. |
| 6,454,799 | B1 | 9/2002 | Schreck |
| 6,458,153 | B1 | 10/2002 | Bailey et al. |
| 6,461,382 | B1 | 10/2002 | Cao |
| 6,468,303 | B1 | 10/2002 | Amplatz et al. |
| 6,468,660 | B2 | 10/2002 | Ogle et al. |
| 6,475,239 | B1 | 11/2002 | Campbell et al. |
| 6,482,228 | B1 | 11/2002 | Norred |
| 6,485,501 | B1 | 11/2002 | Green |
| 6,485,502 | B2 | 11/2002 | Michael et al. |
| 6,488,704 | B1 | 12/2002 | Connelly et al. |
| 6,494,909 | B2 | 12/2002 | Greenhalgh |
| 6,503,272 | B2 | 1/2003 | Duerig et al. |
| 6,508,803 | B1 | 1/2003 | Horikawa et al. |
| 6,508,833 | B2 | 1/2003 | Pavcnik et al. |
| 6,527,800 | B1 | 3/2003 | McGuckin et al. |
| 6,530,949 | B2 | 3/2003 | Konya et al. |
| 6,530,952 | B2 | 3/2003 | Vesely |
| 6,537,297 | B2 | 3/2003 | Tsugita et al. |
| 6,540,768 | B1 | 4/2003 | Diaz et al. |
| 6,540,782 | B1 | 4/2003 | Snyders |
| 6,562,058 | B2 | 5/2003 | Seguin et al. |
| 6,569,196 | B1 | 5/2003 | Vesely |
| 6,572,643 | B1 | 6/2003 | Gharibadeh |
| 6,585,766 | B1 | 7/2003 | Huynh et al. |
| 6,592,546 | B1 | 7/2003 | Barbut et al. |
| 6,592,614 | B2 | 7/2003 | Lenker et al. |
| 6,605,112 | B1 | 8/2003 | Moll et al. |
| 6,610,077 | B1 | 8/2003 | Hancock et al. |
| 6,616,682 | B2 | 9/2003 | Joergensen et al. |
| 6,622,604 | B1 | 9/2003 | Chouinard et al. |
| 6,623,518 | B2 | 9/2003 | Thompson et al. |
| 6,623,521 | B2 | 9/2003 | Steinke et al. |
| 6,626,938 | B1 | 9/2003 | Butaric et al. |
| 6,632,243 | B1 | 10/2003 | Zadno-Azizi et al. |
| 6,635,068 | B1 | 10/2003 | Dubrul et al. |
| 6,635,079 | B2 | 10/2003 | Unsworth et al. |
| 6,635,080 | B1 | 10/2003 | Lauterjung et al. |
| 6,652,571 | B1 | 11/2003 | White et al. |
| 6,652,578 | B2 | 11/2003 | Bailey et al. |
| 6,663,588 | B2 | 12/2003 | DuBois et al. |
| 6,663,663 | B2 | 12/2003 | Kim et al. |
| 6,663,667 | B2 | 12/2003 | Dehdashtian et al. |
| 6,669,724 | B2 | 12/2003 | Park et al. |
| 6,673,089 | B1 | 1/2004 | Yassour et al. |
| 6,673,109 | B2 | 1/2004 | Cox |
| 6,676,668 | B2 | 1/2004 | Mercereau et al. |
| 6,676,692 | B2 | 1/2004 | Rabkin et al. |
| 6,676,698 | B2 | 1/2004 | McGuckin et al. |
| 6,682,543 | B2 | 1/2004 | Barbut et al. |
| 6,682,558 | B2 | 1/2004 | Tu et al. |
| 6,682,559 | B2 | 1/2004 | Myers et al. |
| 6,685,739 | B2 | 2/2004 | DiMatteo et al. |
| 6,689,144 | B2 | 2/2004 | Gerberding |
| 6,689,164 | B1 | 2/2004 | Seguin |
| 6,692,512 | B2 | 2/2004 | Jang |
| 6,695,864 | B2 | 2/2004 | Macoviak et al. |
| 6,695,865 | B2 | 2/2004 | Boyle et al. |
| 6,702,851 | B1 | 3/2004 | Chinn et al. |
| 6,712,842 | B1 | 3/2004 | Gifford et al. |
| 6,712,843 | B2 | 3/2004 | Elliott |
| 6,714,842 | B1 | 3/2004 | Ito |
| 6,719,789 | B2 | 4/2004 | Cox |
| 6,723,116 | B2 | 4/2004 | Taheri |
| 6,729,356 | B1 | 5/2004 | Baker et al. |
| 6,730,118 | B2 | 5/2004 | Spenser et al. |
| 6,730,377 | B2 | 5/2004 | Wang |
| 6,733,525 | B2 | 5/2004 | Yang et al. |
| 6,736,846 | B2 | 5/2004 | Cox |
| 6,752,828 | B2 | 6/2004 | Thornton |
| 6,755,854 | B2 | 6/2004 | Gillick et al. |
| 6,758,855 | B2 | 7/2004 | Fulton et al. |
| 6,764,503 | B1 | 7/2004 | Ishimaru |
| 6,764,509 | B2 | 7/2004 | Chinn et al. |
| 6,767,345 | B2 | 7/2004 | Germain et al. |
| 6,769,434 | B2 | 8/2004 | Liddicoat et al. |
| 6,773,454 | B2 | 8/2004 | Wholey et al. |
| 6,773,456 | B1 | 8/2004 | Gordon et al. |
| 6,776,791 | B1 | 8/2004 | Stallings et al. |
| 6,786,925 | B1 | 9/2004 | Schoon et al. |
| 6,790,229 | B1 | 9/2004 | Berreklouw |
| 6,790,230 | B2 | 9/2004 | Beyersdorf et al. |
| 6,790,237 | B2 | 9/2004 | Stinson |
| 6,792,979 | B2 | 9/2004 | Konya et al. |
| 6,797,002 | B2 | 9/2004 | Spence et al. |
| 6,814,746 | B2 | 11/2004 | Thompson et al. |
| 6,814,754 | B2 | 11/2004 | Greenhalgh |
| 6,821,297 | B2 | 11/2004 | Snyders |
| 6,824,041 | B2 | 11/2004 | Grieder et al. |
| 6,830,585 | B1 | 12/2004 | Artof et al. |
| 6,837,901 | B2 | 1/2005 | Rabkin et al. |
| 6,840,957 | B2 | 1/2005 | DiMatteo et al. |
| 6,843,802 | B1 | 1/2005 | Villalobos et al. |
| 6,849,085 | B2 | 2/2005 | Marton |
| 6,863,668 | B2 | 3/2005 | Gillespie et al. |
| 6,863,688 | B2 | 3/2005 | Ralph et al. |
| 6,866,650 | B2 | 3/2005 | Stevens et al. |
| 6,866,669 | B2 | 3/2005 | Buzzard et al. |
| 6,872,223 | B2 | 3/2005 | Roberts et al. |
| 6,872,226 | B2 | 3/2005 | Cali et al. |
| 6,875,231 | B2 | 4/2005 | Anduiza et al. |
| 6,881,220 | B2 | 4/2005 | Edwin et al. |
| 6,887,266 | B2 | 5/2005 | Williams et al. |
| 6,890,340 | B2 | 5/2005 | Duane |
| 6,893,459 | B1 | 5/2005 | Macoviak |
| 6,893,460 | B2 | 5/2005 | Spenser et al. |
| 6,896,690 | B1 | 5/2005 | Lambrecht et al. |
| 6,905,743 | B1 | 6/2005 | Chen et al. |
| 6,908,481 | B2 | 6/2005 | Cribier |
| 6,911,036 | B2 | 6/2005 | Douk et al. |
| 6,911,040 | B2 | 6/2005 | Johnson et al. |
| 6,911,043 | B2 | 6/2005 | Myers et al. |
| 6,936,058 | B2 | 8/2005 | Forde et al. |
| 6,936,067 | B2 | 8/2005 | Buchanan |
| 6,939,352 | B2 | 9/2005 | Buzzard et al. |
| 6,951,571 | B1 | 10/2005 | Srivastava |
| 6,953,332 | B1 | 10/2005 | Kurk et al. |
| 6,964,673 | B2 | 11/2005 | Tsugita et al. |
| 6,969,395 | B2 | 11/2005 | Eskuri |
| 6,972,025 | B2 | 12/2005 | WasDyke |
| 6,974,464 | B2 | 12/2005 | Quijano et al. |
| 6,974,474 | B2 | 12/2005 | Pavcnik et al. |
| 6,974,476 | B2 | 12/2005 | McGuckin et al. |
| 6,979,350 | B2 | 12/2005 | Moll et al. |
| 6,984,242 | B2 | 1/2006 | Campbell et al. |
| 6,989,027 | B2 | 1/2006 | Allen et al. |
| 7,004,176 | B2 | 2/2006 | Lau |
| 7,011,681 | B2 | 3/2006 | Vesely |
| 7,018,406 | B2 | 3/2006 | Seguin et al. |
| 7,025,791 | B2 | 4/2006 | Levine et al. |
| 7,037,331 | B2 | 5/2006 | Mitelberg et al. |
| 7,041,132 | B2 | 5/2006 | Quijano et al. |
| 7,044,966 | B2 | 5/2006 | Svanidze et al. |
| 7,097,658 | B2 | 8/2006 | Oktay |
| 7,108,715 | B2 | 9/2006 | Lawrence-Brown et al. |
| 7,122,020 | B2 | 10/2006 | Mogul |
| 7,125,418 | B2 | 10/2006 | Duran et al. |
| 7,141,063 | B2 | 11/2006 | White et al. |
| 7,147,663 | B1 | 12/2006 | Berg et al. |
| 7,166,097 | B2 | 1/2007 | Barbut |
| 7,175,652 | B2 | 2/2007 | Cook et al. |
| 7,175,653 | B2 | 2/2007 | Gaber |
| 7,175,654 | B2 | 2/2007 | Bonsignore et al. |
| 7,175,656 | B2 | 2/2007 | Khairkhahan |
| 7,189,258 | B2 | 3/2007 | Johnson et al. |
| 7,191,018 | B2 | 3/2007 | Gielen et al. |
| 7,201,772 | B2 | 4/2007 | Schwammenthal et al. |
| 7,235,093 | B2 | 6/2007 | Gregorich |

(56) References Cited

U.S. PATENT DOCUMENTS

| | | | |
|---|---|---|---|
| 7,252,682 | B2 | 8/2007 | Seguin |
| 7,258,696 | B2 | 8/2007 | Rabkin et al. |
| 7,261,732 | B2 | 8/2007 | Justino |
| 7,264,632 | B2 | 9/2007 | Wright et al. |
| 7,267,686 | B2 | 9/2007 | DiMatteo et al. |
| 7,276,078 | B2 | 10/2007 | Spenser et al. |
| 7,322,932 | B2 | 1/2008 | Xie et al. |
| 7,326,236 | B2 | 2/2008 | Andreas et al. |
| 7,329,279 | B2 | 2/2008 | Haug et al. |
| 7,331,993 | B2 | 2/2008 | White |
| 7,374,560 | B2 | 5/2008 | Ressemann et al. |
| 7,381,219 | B2 | 6/2008 | Salahieh et al. |
| 7,381,220 | B2 | 6/2008 | Macoviak et al. |
| 7,399,315 | B2 | 7/2008 | Tobbi |
| 7,445,631 | B2 | 11/2008 | Salahieh et al. |
| 7,470,285 | B2 | 12/2008 | Nugent et al. |
| 7,491,232 | B2 | 2/2009 | Bolduc et al. |
| 7,510,574 | B2 | 3/2009 | Lê et al. |
| 7,524,330 | B2 | 4/2009 | Berreklouw |
| 7,530,995 | B2 | 5/2009 | Quijano et al. |
| 7,544,206 | B2 | 6/2009 | Cohn |
| 7,622,276 | B2 | 11/2009 | Cunanan et al. |
| 7,628,803 | B2 | 12/2009 | Pavcnik et al. |
| 7,632,298 | B2 | 12/2009 | Hijlkema et al. |
| 7,641,687 | B2 | 1/2010 | Chinn et al. |
| 7,674,282 | B2 | 3/2010 | Wu et al. |
| 7,712,606 | B2 | 5/2010 | Salahieh et al. |
| 7,722,638 | B2 | 5/2010 | Deyette et al. |
| 7,722,662 | B2 | 5/2010 | Steinke et al. |
| 7,722,666 | B2 | 5/2010 | Lafontaine |
| 7,731,742 | B2 | 6/2010 | Schlick et al. |
| 7,736,388 | B2 | 6/2010 | Goldfarb et al. |
| 7,748,389 | B2 | 7/2010 | Salahieh et al. |
| 7,758,625 | B2 | 7/2010 | Wu et al. |
| 7,780,725 | B2 | 8/2010 | Haug et al. |
| 7,799,065 | B2 | 9/2010 | Pappas |
| 7,803,185 | B2 | 9/2010 | Gabbay |
| 7,824,442 | B2 | 11/2010 | Salahieh et al. |
| 7,824,443 | B2 | 11/2010 | Salahieh et al. |
| 7,833,262 | B2 | 11/2010 | McGuckin et al. |
| 7,846,204 | B2 | 12/2010 | Letac et al. |
| 7,857,845 | B2 | 12/2010 | Stacchino et al. |
| 7,892,292 | B2 | 2/2011 | Stack et al. |
| 7,918,880 | B2 | 4/2011 | Austin |
| 7,938,851 | B2 | 5/2011 | Olson et al. |
| 7,959,666 | B2 | 6/2011 | Salahieh et al. |
| 7,959,672 | B2 | 6/2011 | Salahieh et al. |
| 7,988,724 | B2 | 8/2011 | Salahieh et al. |
| 8,048,153 | B2 | 11/2011 | Salahieh et al. |
| 8,052,749 | B2 | 11/2011 | Salahieh et al. |
| 8,136,659 | B2 | 3/2012 | Salahieh et al. |
| 8,157,853 | B2 | 4/2012 | Laske et al. |
| 8,172,896 | B2 | 5/2012 | McNamara et al. |
| 8,182,528 | B2 | 5/2012 | Salahieh et al. |
| 8,192,351 | B2 | 6/2012 | Fishler et al. |
| 8,226,710 | B2 | 7/2012 | Nguyen et al. |
| 8,231,670 | B2 | 7/2012 | Salahieh et al. |
| 8,236,049 | B2 | 8/2012 | Rowe et al. |
| 8,246,678 | B2 | 8/2012 | Salahieh et al. |
| 8,252,051 | B2 | 8/2012 | Chau et al. |
| 8,252,052 | B2 | 8/2012 | Salahieh et al. |
| 8,287,584 | B2 | 10/2012 | Salahieh et al. |
| 8,308,798 | B2 | 11/2012 | Pintor et al. |
| 8,317,858 | B2 | 11/2012 | Straubinger et al. |
| 8,323,335 | B2 | 12/2012 | Rowe et al. |
| 8,328,868 | B2 | 12/2012 | Paul et al. |
| 8,343,213 | B2 | 1/2013 | Salahieh et al. |
| 8,376,865 | B2 | 2/2013 | Forster et al. |
| 8,377,117 | B2 | 2/2013 | Keidar et al. |
| 8,398,708 | B2 | 3/2013 | Meiri et al. |
| 8,403,983 | B2 | 3/2013 | Quadri et al. |
| 8,414,644 | B2 | 4/2013 | Quadri et al. |
| 8,579,962 | B2 | 11/2013 | Salahieh et al. |
| 8,603,160 | B2 | 12/2013 | Salahieh et al. |
| 8,617,236 | B2 | 12/2013 | Paul et al. |
| 8,623,074 | B2 | 1/2014 | Ryan |
| 8,623,076 | B2 | 1/2014 | Salahieh et al. |
| 8,623,078 | B2 | 1/2014 | Salahieh et al. |
| 8,668,733 | B2 | 3/2014 | Haug et al. |
| 8,696,743 | B2 | 4/2014 | Holecek et al. |
| 8,828,078 | B2 | 9/2014 | Salahieh et al. |
| 8,840,662 | B2 | 9/2014 | Salahieh et al. |
| 8,840,663 | B2 | 9/2014 | Salahieh et al. |
| 8,858,620 | B2 | 10/2014 | Salahieh et al. |
| 8,894,703 | B2 | 11/2014 | Salahieh et al. |
| 8,951,299 | B2 | 2/2015 | Paul et al. |
| 8,992,608 | B2 | 3/2015 | Haug et al. |
| 9,005,273 | B2 | 4/2015 | Salahieh et al. |
| 9,011,521 | B2 | 4/2015 | Haug et al. |
| 9,168,131 | B2 | 10/2015 | Yohanan et al. |
| 11,534,295 | B2 | 12/2022 | Mesana et al. |
| 2001/0002445 | A1 | 5/2001 | Vesely |
| 2001/0007956 | A1 | 7/2001 | Letac et al. |
| 2001/0010017 | A1 | 7/2001 | Letac et al. |
| 2001/0021872 | A1 | 9/2001 | Bailey et al. |
| 2001/0025196 | A1 | 9/2001 | Chinn et al. |
| 2001/0027338 | A1 | 10/2001 | Greenberg |
| 2001/0032013 | A1 | 10/2001 | Marton |
| 2001/0039450 | A1 | 11/2001 | Pavcnik et al. |
| 2001/0041928 | A1 | 11/2001 | Pavcnik et al. |
| 2001/0041930 | A1 | 11/2001 | Globerman et al. |
| 2001/0044634 | A1 | 11/2001 | Michael et al. |
| 2001/0044652 | A1 | 11/2001 | Moore |
| 2001/0044656 | A1 | 11/2001 | Williamson et al. |
| 2002/0002396 | A1 | 1/2002 | Fulkerson |
| 2002/0010489 | A1 | 1/2002 | Grayzel et al. |
| 2002/0026233 | A1 | 2/2002 | Shaknovich |
| 2002/0029014 | A1 | 3/2002 | Jayaraman |
| 2002/0029981 | A1 | 3/2002 | Nigam |
| 2002/0032480 | A1 | 3/2002 | Spence et al. |
| 2002/0032481 | A1 | 3/2002 | Gabbay |
| 2002/0042651 | A1 | 4/2002 | Liddicoat et al. |
| 2002/0052651 | A1 | 5/2002 | Myers et al. |
| 2002/0055767 | A1 | 5/2002 | Forde et al. |
| 2002/0055769 | A1 | 5/2002 | Wang |
| 2002/0055774 | A1 | 5/2002 | Liddicoat |
| 2002/0058987 | A1 | 5/2002 | Butaric et al. |
| 2002/0058995 | A1 | 5/2002 | Stevens |
| 2002/0077696 | A1 | 6/2002 | Zadno-Azizi et al. |
| 2002/0082609 | A1 | 6/2002 | Green |
| 2002/0095173 | A1 | 7/2002 | Mazzocchi et al. |
| 2002/0095209 | A1 | 7/2002 | Zadno-Azizi et al. |
| 2002/0111674 | A1 | 8/2002 | Chouinard et al. |
| 2002/0120328 | A1 | 8/2002 | Pathak et al. |
| 2002/0123802 | A1 | 9/2002 | Snyders |
| 2002/0138138 | A1 | 9/2002 | Yang |
| 2002/0151970 | A1 | 10/2002 | Garrison et al. |
| 2002/0156522 | A1 | 10/2002 | Ivancev et al. |
| 2002/0161390 | A1 | 10/2002 | Mouw |
| 2002/0161392 | A1 | 10/2002 | Dubrul |
| 2002/0161394 | A1 | 10/2002 | Macoviak et al. |
| 2002/0165576 | A1 | 11/2002 | Boyle et al. |
| 2002/0177766 | A1 | 11/2002 | Mogul |
| 2002/0183781 | A1 | 12/2002 | Casey et al. |
| 2002/0188341 | A1 | 12/2002 | Elliott |
| 2002/0188344 | A1 | 12/2002 | Bolea et al. |
| 2002/0193871 | A1 | 12/2002 | Beyersdorf et al. |
| 2003/0014104 | A1 | 1/2003 | Cribier |
| 2003/0023303 | A1 | 1/2003 | Palmaz et al. |
| 2003/0028247 | A1 | 2/2003 | Cali |
| 2003/0036791 | A1 | 2/2003 | Philipp et al. |
| 2003/0040736 | A1 | 2/2003 | Stevens et al. |
| 2003/0040771 | A1 | 2/2003 | Hyodoh et al. |
| 2003/0040772 | A1 | 2/2003 | Hyodoh et al. |
| 2003/0040791 | A1 | 2/2003 | Oktay |
| 2003/0040792 | A1 | 2/2003 | Gabbay |
| 2003/0050694 | A1 | 3/2003 | Yang et al. |
| 2003/0055495 | A1 | 3/2003 | Pease et al. |
| 2003/0057156 | A1 | 3/2003 | Peterson et al. |
| 2003/0060844 | A1 | 3/2003 | Borillo et al. |
| 2003/0069492 | A1 | 4/2003 | Abrams et al. |
| 2003/0069646 | A1 | 4/2003 | Stinson |
| 2003/0070944 | A1 | 4/2003 | Nigam |
| 2003/0074058 | A1 | 4/2003 | Sherry |

(56) References Cited

U.S. PATENT DOCUMENTS

| | | | |
|---|---|---|---|
| 2003/0093145 | A1 | 5/2003 | Lawrence-Brown et al. |
| 2003/0100918 | A1 | 5/2003 | Duane |
| 2003/0100919 | A1 | 5/2003 | Hopkins et al. |
| 2003/0109924 | A1 | 6/2003 | Cribier |
| 2003/0109930 | A1 | 6/2003 | Bluni et al. |
| 2003/0114912 | A1 | 6/2003 | Sequin et al. |
| 2003/0114913 | A1 | 6/2003 | Spenser et al. |
| 2003/0125795 | A1 | 7/2003 | Pavcnik et al. |
| 2003/0130729 | A1 | 7/2003 | Paniagua et al. |
| 2003/0135257 | A1 | 7/2003 | Taheri |
| 2003/0144732 | A1 | 7/2003 | Cosgrove et al. |
| 2003/0149475 | A1 | 8/2003 | Hyodoh et al. |
| 2003/0149476 | A1 | 8/2003 | Damm et al. |
| 2003/0149478 | A1 | 8/2003 | Figulla et al. |
| 2003/0153974 | A1 | 8/2003 | Spenser et al. |
| 2003/0165352 | A1 | 9/2003 | Ibrahim et al. |
| 2003/0171803 | A1 | 9/2003 | Shimon |
| 2003/0176884 | A1 | 9/2003 | Berrada et al. |
| 2003/0181850 | A1 | 9/2003 | Diamond et al. |
| 2003/0187495 | A1 | 10/2003 | Cully et al. |
| 2003/0191516 | A1 | 10/2003 | Weldon et al. |
| 2003/0195609 | A1 | 10/2003 | Berenstein et al. |
| 2003/0199759 | A1 | 10/2003 | Richard |
| 2003/0199913 | A1 | 10/2003 | Dubrul et al. |
| 2003/0199971 | A1 | 10/2003 | Tower et al. |
| 2003/0199972 | A1 | 10/2003 | Zadno-Azizi et al. |
| 2003/0204249 | A1 | 10/2003 | Letort |
| 2003/0208224 | A1 | 11/2003 | Broome |
| 2003/0212429 | A1 | 11/2003 | Keegan et al. |
| 2003/0212452 | A1 | 11/2003 | Zadno-Azizi et al. |
| 2003/0212454 | A1 | 11/2003 | Scott et al. |
| 2003/0216774 | A1 | 11/2003 | Larson |
| 2003/0225445 | A1 | 12/2003 | Derus et al. |
| 2003/0229390 | A1 | 12/2003 | Ashton et al. |
| 2003/0233117 | A1 | 12/2003 | Adams et al. |
| 2003/0236567 | A1 | 12/2003 | Elliot |
| 2004/0019374 | A1 | 1/2004 | Hojeibane et al. |
| 2004/0033364 | A1 | 2/2004 | Spiridigliozzi et al. |
| 2004/0034411 | A1 | 2/2004 | Quijano et al. |
| 2004/0039436 | A1 | 2/2004 | Spenser et al. |
| 2004/0049224 | A1 | 3/2004 | Buehlmann et al. |
| 2004/0049226 | A1 | 3/2004 | Keegan et al. |
| 2004/0049262 | A1 | 3/2004 | Obermiller et al. |
| 2004/0049266 | A1 | 3/2004 | Anduiza et al. |
| 2004/0059409 | A1 | 3/2004 | Stenzel |
| 2004/0073198 | A1 | 4/2004 | Gilson et al. |
| 2004/0082904 | A1 | 4/2004 | Houde et al. |
| 2004/0082967 | A1 | 4/2004 | Broome et al. |
| 2004/0082989 | A1 | 4/2004 | Cook et al. |
| 2004/0087982 | A1 | 5/2004 | Eskuri |
| 2004/0088045 | A1 | 5/2004 | Cox |
| 2004/0093016 | A1 | 5/2004 | Root et al. |
| 2004/0093060 | A1 | 5/2004 | Seguin et al. |
| 2004/0097788 | A1 | 5/2004 | Mourlas et al. |
| 2004/0098022 | A1 | 5/2004 | Barone |
| 2004/0098098 | A1 | 5/2004 | McGuckin et al. |
| 2004/0098099 | A1 | 5/2004 | McCullagh et al. |
| 2004/0098112 | A1 | 5/2004 | DiMatteo et al. |
| 2004/0107004 | A1 | 6/2004 | Levine et al. |
| 2004/0111096 | A1 | 6/2004 | Tu et al. |
| 2004/0116951 | A1 | 6/2004 | Rosengart |
| 2004/0116999 | A1 | 6/2004 | Ledergerber |
| 2004/0117004 | A1 | 6/2004 | Osborne et al. |
| 2004/0117009 | A1 | 6/2004 | Cali et al. |
| 2004/0122468 | A1 | 6/2004 | Yodfat et al. |
| 2004/0122516 | A1 | 6/2004 | Fogarty et al. |
| 2004/0127936 | A1 | 7/2004 | Salahieh et al. |
| 2004/0127979 | A1 | 7/2004 | Wilson et al. |
| 2004/0133274 | A1 | 7/2004 | Webler et al. |
| 2004/0138694 | A1 | 7/2004 | Tran et al. |
| 2004/0138742 | A1 | 7/2004 | Myers et al. |
| 2004/0138743 | A1 | 7/2004 | Myers et al. |
| 2004/0148018 | A1 | 7/2004 | Carpentier et al. |
| 2004/0148021 | A1 | 7/2004 | Cartledge et al. |
| 2004/0153094 | A1 | 8/2004 | Dunfee et al. |
| 2004/0158277 | A1 | 8/2004 | Lowe et al. |
| 2004/0167565 | A1 | 8/2004 | Beulke et al. |
| 2004/0167620 | A1 | 8/2004 | Ortiz et al. |
| 2004/0181140 | A1 | 9/2004 | Falwell et al. |
| 2004/0186558 | A1 | 9/2004 | Pavcnik et al. |
| 2004/0186563 | A1 | 9/2004 | Lobbi |
| 2004/0193261 | A1 | 9/2004 | Berreklouw |
| 2004/0197695 | A1 | 10/2004 | Aono |
| 2004/0199245 | A1 | 10/2004 | Lauterjung |
| 2004/0204755 | A1 | 10/2004 | Robin |
| 2004/0210304 | A1 | 10/2004 | Seguin et al. |
| 2004/0210306 | A1 | 10/2004 | Quijano et al. |
| 2004/0210307 | A1 | 10/2004 | Khairkhahan |
| 2004/0215331 | A1 | 10/2004 | Chew et al. |
| 2004/0215333 | A1 | 10/2004 | Duran et al. |
| 2004/0215339 | A1 | 10/2004 | Drasler et al. |
| 2004/0220655 | A1 | 11/2004 | Swanson et al. |
| 2004/0225321 | A1 | 11/2004 | Krolik et al. |
| 2004/0225353 | A1 | 11/2004 | McGuckin et al. |
| 2004/0225354 | A1 | 11/2004 | Allen et al. |
| 2004/0225355 | A1 | 11/2004 | Stevens |
| 2004/0243221 | A1 | 12/2004 | Fawzi et al. |
| 2004/0254636 | A1 | 12/2004 | Flagle et al. |
| 2004/0260390 | A1 | 12/2004 | Sarac et al. |
| 2005/0010287 | A1 | 1/2005 | Macoviak et al. |
| 2005/0021136 | A1 | 1/2005 | Xie et al. |
| 2005/0033398 | A1 | 2/2005 | Seguin |
| 2005/0033402 | A1 | 2/2005 | Cully et al. |
| 2005/0043711 | A1 | 2/2005 | Corcoran et al. |
| 2005/0043757 | A1 | 2/2005 | Arad et al. |
| 2005/0043790 | A1 | 2/2005 | Seguin |
| 2005/0049692 | A1 | 3/2005 | Numamoto et al. |
| 2005/0049696 | A1 | 3/2005 | Siess et al. |
| 2005/0055088 | A1 | 3/2005 | Liddicoat et al. |
| 2005/0060016 | A1 | 3/2005 | Wu et al. |
| 2005/0060029 | A1 | 3/2005 | Le et al. |
| 2005/0065594 | A1 | 3/2005 | DiMatteo et al. |
| 2005/0075584 | A1 | 4/2005 | Cali |
| 2005/0075662 | A1 | 4/2005 | Pedersen et al. |
| 2005/0075712 | A1 | 4/2005 | Biancucci et al. |
| 2005/0075717 | A1 | 4/2005 | Nguyen et al. |
| 2005/0075719 | A1 | 4/2005 | Bergheim |
| 2005/0075724 | A1 | 4/2005 | Svanidze et al. |
| 2005/0075730 | A1 | 4/2005 | Myers et al. |
| 2005/0075731 | A1 | 4/2005 | Artof et al. |
| 2005/0085841 | A1 | 4/2005 | Eversull et al. |
| 2005/0085842 | A1 | 4/2005 | Eversull et al. |
| 2005/0085843 | A1 | 4/2005 | Opolski et al. |
| 2005/0085890 | A1 | 4/2005 | Rasmussen et al. |
| 2005/0090846 | A1 | 4/2005 | Pedersen et al. |
| 2005/0090890 | A1 | 4/2005 | Wu et al. |
| 2005/0096692 | A1 | 5/2005 | Linder et al. |
| 2005/0096734 | A1 | 5/2005 | Majercak et al. |
| 2005/0096735 | A1 | 5/2005 | Hojeibane et al. |
| 2005/0096736 | A1 | 5/2005 | Osse et al. |
| 2005/0096738 | A1 | 5/2005 | Cali et al. |
| 2005/0100580 | A1 | 5/2005 | Osborne et al. |
| 2005/0107822 | A1 | 5/2005 | WasDyke |
| 2005/0113910 | A1 | 5/2005 | Paniagua et al. |
| 2005/0131438 | A1 | 6/2005 | Cohn |
| 2005/0137683 | A1 | 6/2005 | Hezi-Yamit et al. |
| 2005/0137686 | A1 | 6/2005 | Salahieh et al. |
| 2005/0137687 | A1 | 6/2005 | Salahieh et al. |
| 2005/0137688 | A1 | 6/2005 | Salahieh et al. |
| 2005/0137689 | A1 | 6/2005 | Salahieh et al. |
| 2005/0137690 | A1 | 6/2005 | Salahieh et al. |
| 2005/0137691 | A1 | 6/2005 | Salahieh et al. |
| 2005/0137692 | A1 | 6/2005 | Haug et al. |
| 2005/0137693 | A1 | 6/2005 | Haug et al. |
| 2005/0137694 | A1 | 6/2005 | Haug et al. |
| 2005/0137695 | A1 | 6/2005 | Salahieh et al. |
| 2005/0137696 | A1 | 6/2005 | Salahieh et al. |
| 2005/0137697 | A1 | 6/2005 | Salahieh et al. |
| 2005/0137698 | A1 | 6/2005 | Salahieh et al. |
| 2005/0137699 | A1 | 6/2005 | Salahieh et al. |
| 2005/0137701 | A1 | 6/2005 | Salahieh et al. |
| 2005/0137702 | A1 | 6/2005 | Haug et al. |
| 2005/0138689 | A1 | 6/2005 | Aukerman |
| 2005/0143807 | A1 | 6/2005 | Pavcnik et al. |

(56) References Cited

U.S. PATENT DOCUMENTS

| | | | |
|---|---|---|---|
| 2005/0143809 | A1 | 6/2005 | Salahieh et al. |
| 2005/0149159 | A1 | 7/2005 | Andreas et al. |
| 2005/0165352 | A1 | 7/2005 | Henry et al. |
| 2005/0165477 | A1 | 7/2005 | Anduiza et al. |
| 2005/0165479 | A1 | 7/2005 | Drews et al. |
| 2005/0182486 | A1 | 8/2005 | Gabbay |
| 2005/0197694 | A1 | 9/2005 | Pai et al. |
| 2005/0197695 | A1 | 9/2005 | Stacchino et al. |
| 2005/0203549 | A1 | 9/2005 | Realyvasquez |
| 2005/0203614 | A1 | 9/2005 | Forster et al. |
| 2005/0203615 | A1 | 9/2005 | Forster et al. |
| 2005/0203616 | A1 | 9/2005 | Cribier |
| 2005/0203617 | A1 | 9/2005 | Forster et al. |
| 2005/0203618 | A1 | 9/2005 | Sharkawy et al. |
| 2005/0203818 | A9 | 9/2005 | Rotman et al. |
| 2005/0209580 | A1 | 9/2005 | Freyman |
| 2005/0228472 | A1 | 10/2005 | Case et al. |
| 2005/0228495 | A1 | 10/2005 | Macoviak |
| 2005/0234546 | A1 | 10/2005 | Nugent et al. |
| 2005/0240200 | A1 | 10/2005 | Bergheim |
| 2005/0240262 | A1 | 10/2005 | White |
| 2005/0251250 | A1 | 11/2005 | Verhoeven et al. |
| 2005/0251251 | A1 | 11/2005 | Cribier |
| 2005/0261759 | A1 | 11/2005 | Lambrecht et al. |
| 2005/0267560 | A1 | 12/2005 | Bates |
| 2005/0283231 | A1 | 12/2005 | Haug et al. |
| 2005/0283962 | A1 | 12/2005 | Boudjemline |
| 2006/0004439 | A1 | 1/2006 | Spenser et al. |
| 2006/0004442 | A1 | 1/2006 | Spenser et al. |
| 2006/0015168 | A1 | 1/2006 | Gunderson |
| 2006/0025857 | A1 | 2/2006 | Bergheim et al. |
| 2006/0058872 | A1 | 3/2006 | Salahieh et al. |
| 2006/0149360 | A1 | 7/2006 | Schwammenthal et al. |
| 2006/0155312 | A1 | 7/2006 | Levine et al. |
| 2006/0161249 | A1 | 7/2006 | Realyvasquez et al. |
| 2006/0173524 | A1 | 8/2006 | Salahieh et al. |
| 2006/0195183 | A1 | 8/2006 | Navia et al. |
| 2006/0253191 | A1 | 11/2006 | Salahieh et al. |
| 2006/0259134 | A1 | 11/2006 | Schwammenthal et al. |
| 2006/0271166 | A1 | 11/2006 | Thill et al. |
| 2006/0287668 | A1 | 12/2006 | Fawzi et al. |
| 2006/0287717 | A1 | 12/2006 | Rowe et al. |
| 2007/0010876 | A1 | 1/2007 | Salahieh et al. |
| 2007/0010877 | A1 | 1/2007 | Salahieh et al. |
| 2007/0016286 | A1 | 1/2007 | Herrmann et al. |
| 2007/0055340 | A1 | 3/2007 | Pryor |
| 2007/0061008 | A1 | 3/2007 | Salahieh et al. |
| 2007/0112355 | A1 | 5/2007 | Salahieh et al. |
| 2007/0118214 | A1 | 5/2007 | Salahieh et al. |
| 2007/0162107 | A1 | 7/2007 | Haug et al. |
| 2007/0173918 | A1 | 7/2007 | Dreher et al. |
| 2007/0203503 | A1 | 8/2007 | Salahieh et al. |
| 2007/0244552 | A1 | 10/2007 | Salahieh et al. |
| 2007/0288089 | A1 | 12/2007 | Gurskis et al. |
| 2008/0009940 | A1 | 1/2008 | Cribier |
| 2008/0033541 | A1 | 2/2008 | Gelbart et al. |
| 2008/0071363 | A1 | 3/2008 | Tuval et al. |
| 2008/0082165 | A1 | 4/2008 | Wilson et al. |
| 2008/0125859 | A1 | 5/2008 | Salahieh et al. |
| 2008/0188928 | A1 | 8/2008 | Salahieh et al. |
| 2008/0208328 | A1 | 8/2008 | Antocci et al. |
| 2008/0208332 | A1 | 8/2008 | Lamphere et al. |
| 2008/0221672 | A1 | 9/2008 | Lamphere et al. |
| 2008/0234814 | A1 | 9/2008 | Salahieh et al. |
| 2008/0255661 | A1 | 10/2008 | Straubinger et al. |
| 2008/0269878 | A1 | 10/2008 | Iobbi |
| 2008/0288054 | A1 | 11/2008 | Pulnev et al. |
| 2009/0005863 | A1 | 1/2009 | Goetz et al. |
| 2009/0030512 | A1 | 1/2009 | Thielen et al. |
| 2009/0054969 | A1 | 2/2009 | Salahieh et al. |
| 2009/0076598 | A1 | 3/2009 | Salahieh et al. |
| 2009/0093877 | A1 | 4/2009 | Keidar et al. |
| 2009/0171456 | A1 | 7/2009 | Kveen et al. |
| 2009/0216312 | A1 | 8/2009 | Straubinger et al. |
| 2009/0222076 | A1 | 9/2009 | Figulla et al. |
| 2009/0264759 | A1 | 10/2009 | Byrd |
| 2009/0264997 | A1 | 10/2009 | Salahieh et al. |
| 2009/0299462 | A1 | 12/2009 | Fawzi et al. |
| 2010/0036479 | A1 | 2/2010 | Hill et al. |
| 2010/0049313 | A1 | 2/2010 | Alon et al. |
| 2010/0082089 | A1 | 4/2010 | Quadri et al. |
| 2010/0094399 | A1 | 4/2010 | Dorn et al. |
| 2010/0121434 | A1 | 5/2010 | Paul et al. |
| 2010/0161045 | A1 | 6/2010 | Righini |
| 2010/0185275 | A1 | 7/2010 | Richter et al. |
| 2010/0191320 | A1 | 7/2010 | Straubinger et al. |
| 2010/0191326 | A1 | 7/2010 | Alkhatib |
| 2010/0219092 | A1 | 9/2010 | Salahieh et al. |
| 2010/0249908 | A1 | 9/2010 | Chau et al. |
| 2010/0280495 | A1 | 11/2010 | Paul et al. |
| 2010/0298931 | A1 | 11/2010 | Quadri et al. |
| 2011/0257735 | A1 | 10/2011 | Salahieh et al. |
| 2011/0264196 | A1 | 10/2011 | Savage et al. |
| 2011/0276129 | A1 | 11/2011 | Salahieh et al. |
| 2011/0288634 | A1 | 11/2011 | Tuval et al. |
| 2011/0295363 | A1 | 12/2011 | Girard et al. |
| 2012/0016469 | A1 | 1/2012 | Salahieh et al. |
| 2012/0016471 | A1 | 1/2012 | Salahieh et al. |
| 2012/0022642 | A1 | 1/2012 | Haug et al. |
| 2012/0029627 | A1 | 2/2012 | Salahieh et al. |
| 2012/0041549 | A1 | 2/2012 | Salahieh et al. |
| 2012/0041550 | A1 | 2/2012 | Salahieh et al. |
| 2012/0046740 | A1 | 2/2012 | Paul et al. |
| 2012/0053683 | A1 | 3/2012 | Salahieh et al. |
| 2012/0089224 | A1 | 4/2012 | Haug et al. |
| 2012/0132547 | A1 | 5/2012 | Salahieh et al. |
| 2012/0179244 | A1 | 7/2012 | Schankereli et al. |
| 2012/0197379 | A1 | 8/2012 | Laske et al. |
| 2012/0303113 | A1 | 11/2012 | Benichou et al. |
| 2012/0303116 | A1 | 11/2012 | Gorman et al. |
| 2012/0310334 | A1 | 12/2012 | Dolan |
| 2012/0330409 | A1 | 12/2012 | Haug et al. |
| 2013/0013057 | A1 | 1/2013 | Salahieh et al. |
| 2013/0018457 | A1 | 1/2013 | Gregg et al. |
| 2013/0030520 | A1 | 1/2013 | Lee et al. |
| 2013/0079867 | A1 | 3/2013 | Hoffman et al. |
| 2013/0079869 | A1 | 3/2013 | Straubinger et al. |
| 2013/0096664 | A1 | 4/2013 | Goetz et al. |
| 2013/0123796 | A1 | 5/2013 | Sutton et al. |
| 2013/0138207 | A1 | 5/2013 | Quadri et al. |
| 2013/0158656 | A1 | 6/2013 | Sutton et al. |
| 2013/0184813 | A1 | 7/2013 | Quadri et al. |
| 2013/0190865 | A1 | 7/2013 | Anderson |
| 2013/0282101 | A1* | 10/2013 | Eidenschink ............ A61F 2/06 623/1.12 |
| 2013/0304199 | A1 | 11/2013 | Sutton et al. |
| 2014/0018911 | A1 | 1/2014 | Zhou et al. |
| 2014/0094904 | A1 | 4/2014 | Salahieh et al. |
| 2014/0114405 | A1 | 4/2014 | Paul et al. |
| 2014/0114406 | A1 | 4/2014 | Salahieh et al. |
| 2014/0121766 | A1 | 5/2014 | Salahieh et al. |
| 2014/0135912 | A1 | 5/2014 | Salahieh et al. |
| 2014/0243967 | A1 | 8/2014 | Salahieh et al. |
| 2015/0012085 | A1 | 1/2015 | Salahieh et al. |
| 2015/0073540 | A1 | 3/2015 | Salahieh et al. |
| 2015/0073541 | A1 | 3/2015 | Salahieh et al. |
| 2015/0127094 | A1 | 5/2015 | Salahieh et al. |
| 2016/0045307 | A1 | 2/2016 | Yohanan et al. |
| 2016/0199184 | A1 | 7/2016 | Ma et al. |
| 2016/0220367 | A1* | 8/2016 | Barrett ................. A61F 2/2436 |
| 2016/0302948 | A1 | 10/2016 | Majano |
| 2018/0214267 | A1 | 8/2018 | Lally et al. |

FOREIGN PATENT DOCUMENTS

| | | | |
|---|---|---|---|
| DE | 19532846 | A1 | 3/1997 |
| DE | 19546692 | A1 | 6/1997 |
| DE | 19857887 | A1 | 7/2000 |
| DE | 19907646 | A1 | 8/2000 |
| DE | 10049812 | A1 | 4/2002 |
| DE | 10049813 | C1 | 4/2002 |
| DE | 10049814 | A1 | 4/2002 |
| DE | 10049815 | A1 | 4/2002 |
| EP | 0103546 | B1 | 5/1988 |

(56) References Cited

FOREIGN PATENT DOCUMENTS

| | | | |
|---|---|---|---|
| EP | 0144167 | B1 | 11/1989 |
| EP | 579523 | A1 | 1/1994 |
| EP | 0409929 | B1 | 4/1997 |
| EP | 0850607 | A1 | 7/1998 |
| EP | 0597967 | B1 | 12/1999 |
| EP | 1000590 | A1 | 5/2000 |
| EP | 1057459 | A1 | 12/2000 |
| EP | 1057460 | A1 | 12/2000 |
| EP | 1078610 | A2 | 2/2001 |
| EP | 1088529 | A2 | 4/2001 |
| EP | 0937439 | B1 | 9/2003 |
| EP | 1340473 | A2 | 9/2003 |
| EP | 1356793 | A3 | 3/2004 |
| EP | 1042045 | B1 | 5/2004 |
| EP | 0819013 | B1 | 6/2004 |
| EP | 1430853 | A2 | 6/2004 |
| EP | 1435879 | A1 | 7/2004 |
| EP | 1439800 | A2 | 7/2004 |
| EP | 1469797 | A1 | 10/2004 |
| EP | 1472996 | A1 | 11/2004 |
| EP | 1229864 | B1 | 4/2005 |
| EP | 1059894 | B1 | 7/2005 |
| EP | 1551274 | A2 | 7/2005 |
| EP | 1551336 | A1 | 7/2005 |
| EP | 1562515 | A1 | 8/2005 |
| EP | 1570809 | A1 | 9/2005 |
| EP | 1576937 | A2 | 9/2005 |
| EP | 1582178 | A2 | 10/2005 |
| EP | 1582179 | A2 | 10/2005 |
| EP | 1589902 | A1 | 11/2005 |
| EP | 1600121 | A1 | 11/2005 |
| EP | 1156757 | B1 | 12/2005 |
| EP | 1616531 | A2 | 1/2006 |
| EP | 1690515 | A1 | 8/2006 |
| EP | 1605871 | B1 | 7/2008 |
| EP | 2047824 | B2 | 5/2012 |
| EP | 2749254 | B1 | 6/2015 |
| EP | 2926766 | A1 | 10/2015 |
| FR | 2788217 | A1 | 7/2000 |
| GB | 2056023 | A | 3/1981 |
| GB | 2398245 | A | 8/2004 |
| SU | 1271508 | A1 | 11/1986 |
| SU | 1371700 | A1 | 2/1988 |
| WO | 9117720 | A1 | 11/1991 |
| WO | 9217118 | A1 | 10/1992 |
| WO | 9301768 | A1 | 2/1993 |
| WO | 9315693 | A1 | 8/1993 |
| WO | 9504556 | A2 | 2/1995 |
| WO | 9529640 | A1 | 11/1995 |
| WO | 9614032 | A1 | 5/1996 |
| WO | 9624306 | A1 | 8/1996 |
| WO | 9640012 | A1 | 12/1996 |
| WO | 9748350 | A1 | 12/1997 |
| WO | 9829057 | A1 | 7/1998 |
| WO | 9836790 | A1 | 8/1998 |
| WO | 9850103 | A1 | 11/1998 |
| WO | 9855047 | A1 | 12/1998 |
| WO | 9857599 | A2 | 12/1998 |
| WO | 9933414 | A1 | 7/1999 |
| WO | 9940964 | A1 | 8/1999 |
| WO | 9944542 | A2 | 9/1999 |
| WO | 9947075 | A1 | 9/1999 |
| WO | 9951165 | A1 | 10/1999 |
| WO | 0009059 | A2 | 2/2000 |
| WO | 0041652 | A1 | 7/2000 |
| WO | 0044308 | A2 | 8/2000 |
| WO | 0044311 | A2 | 8/2000 |
| WO | 0044313 | A1 | 8/2000 |
| WO | 0045874 | A1 | 8/2000 |
| WO | 0047139 | A1 | 8/2000 |
| WO | 0049970 | A1 | 8/2000 |
| WO | 0067661 | A2 | 11/2000 |
| WO | 0105331 | A1 | 1/2001 |
| WO | 0106959 | A1 | 2/2001 |
| WO | 0108596 | A1 | 2/2001 |
| WO | 0110320 | A1 | 2/2001 |
| WO | 0110343 | A1 | 2/2001 |
| WO | 0135870 | A1 | 5/2001 |
| WO | 0149213 | A2 | 7/2001 |
| WO | 0154625 | A1 | 8/2001 |
| WO | 0162189 | A1 | 8/2001 |
| WO | 0164137 | A1 | 9/2001 |
| WO | 0176510 | A2 | 10/2001 |
| WO | 0197715 | A1 | 12/2001 |
| WO | 0236048 | A1 | 5/2002 |
| WO | 0241789 | A2 | 5/2002 |
| WO | 0243620 | A1 | 6/2002 |
| WO | 0247575 | A2 | 6/2002 |
| WO | 02056955 | A1 | 7/2002 |
| WO | 02069842 | A2 | 9/2002 |
| WO | 02100297 | A2 | 12/2002 |
| WO | 03003943 | A2 | 1/2003 |
| WO | 03003949 | A2 | 1/2003 |
| WO | 03007222 | A1 | 1/2003 |
| WO | 03011195 | A2 | 2/2003 |
| WO | 03015851 | A1 | 2/2003 |
| WO | 03028592 | A1 | 4/2003 |
| WO | 03030776 | A2 | 4/2003 |
| WO | 03032869 | A1 | 4/2003 |
| WO | 03037222 | A2 | 5/2003 |
| WO | 03037227 | A2 | 5/2003 |
| WO | 03047468 | A1 | 6/2003 |
| WO | 03047648 | A2 | 6/2003 |
| WO | 03088873 | A1 | 10/2003 |
| WO | 03094793 | A1 | 11/2003 |
| WO | 03094797 | A1 | 11/2003 |
| WO | 03096932 | A1 | 11/2003 |
| WO | 2004006803 | A1 | 1/2004 |
| WO | 2004014256 | A1 | 1/2004 |
| WO | 2004006804 | A1 | 2/2004 |
| WO | 2004019817 | A1 | 3/2004 |
| WO | 2004021922 | A2 | 3/2004 |
| WO | 2004023980 | A2 | 3/2004 |
| WO | 2004019811 | A9 | 4/2004 |
| WO | 2004026117 | A2 | 4/2004 |
| WO | 2004041126 | A1 | 5/2004 |
| WO | 2004043293 | A2 | 5/2004 |
| WO | 2004047681 | A1 | 6/2004 |
| WO | 2004058106 | A2 | 8/2004 |
| WO | 2004066876 | A1 | 8/2004 |
| WO | 2004082536 | A1 | 9/2004 |
| WO | 2004089250 | A1 | 10/2004 |
| WO | 2004089253 | A1 | 10/2004 |
| WO | 2004093728 | A2 | 11/2004 |
| WO | 2004105651 | A1 | 12/2004 |
| WO | 2005002466 | A2 | 1/2005 |
| WO | 2005004753 | A1 | 1/2005 |
| WO | 2005009285 | A2 | 2/2005 |
| WO | 2005011534 | A1 | 2/2005 |
| WO | 2005011535 | A2 | 2/2005 |
| WO | 2005023155 | A1 | 3/2005 |
| WO | 2005027790 | A1 | 3/2005 |
| WO | 2005046528 | A1 | 5/2005 |
| WO | 2005046529 | A1 | 5/2005 |
| WO | 2005048883 | A1 | 6/2005 |
| WO | 2005065585 | A1 | 7/2005 |
| WO | 2005084595 | A1 | 9/2005 |
| WO | 2005087140 | A1 | 9/2005 |
| WO | 2005096993 | A1 | 10/2005 |
| WO | 2006005015 | A2 | 1/2006 |
| WO | 2006009690 | A1 | 1/2006 |
| WO | 2006027499 | A2 | 3/2006 |
| WO | 2005062980 | A3 | 5/2006 |
| WO | 2006093795 | A1 | 9/2006 |
| WO | 2006138391 | A2 | 12/2006 |
| WO | 2007009117 | A1 | 1/2007 |
| WO | 2007033093 | A2 | 3/2007 |
| WO | 2007035471 | A2 | 3/2007 |
| WO | 2005102015 | A3 | 4/2007 |
| WO | 2007044285 | A2 | 4/2007 |
| WO | 2007058847 | A2 | 5/2007 |
| WO | 2007092354 | A2 | 8/2007 |
| WO | 2007097983 | A2 | 8/2007 |
| WO | 2007053243 | A2 | 9/2007 |

(56) References Cited

FOREIGN PATENT DOCUMENTS

| | | | |
|---|---|---|---|
| WO | 2008028569 | A1 | 3/2008 |
| WO | 2008035337 | A2 | 3/2008 |
| WO | 2010042950 | A2 | 4/2010 |
| WO | 2010098857 | A1 | 9/2010 |
| WO | 2012116368 | A2 | 8/2012 |
| WO | 2012162228 | A1 | 11/2012 |
| WO | 2013009975 | A1 | 1/2013 |
| WO | 2013028387 | A2 | 2/2013 |
| WO | 2013074671 | A1 | 5/2013 |
| WO | 2013096545 | A1 | 6/2013 |
| WO | 2016126511 | A2 | 8/2016 |

OTHER PUBLICATIONS

US 8,062,357 B2, 11/2011, Salahieh et al. (withdrawn)
US 8,075,614 B2, 12/2011, Salahieh et al. (withdrawn)
US 8,133,271 B2, 03/2012, Salahieh et al. (withdrawn)
US 8,211,170 B2, 07/2012, Paul et al. (withdrawn)
International Search Report and Written Opinion for International Application No. PCT/US2024/018748, dated Jun. 27, 2024. (13 pages).
Cribier et al., "Percutaneous Transluminal Valvuloplasty of Acquired Aortic Stenosis in Elderly Patients: An Alternative to Valve Replacement?" The Lancet, 63-7 (Jan. 11, 1986).
Supplemental Search Report from EP Patent Office, EP Application No. 04813777.2, Aug. 19, 2011.
Laborde et al., "Percutaneous Implantation of the Corevalve Aortic Valve Prosthesis for Patients Presenting High Risk for Surgical Valve Replacement." EuroIntervention: 472-474, Feb. 2006.
"A Matter of Size." Triennial Review of the National Nanotechnology Initiative, The National Academies Press, Washington DC, v-13, http://www.nap.edu/catalog/11752/a-matter-of-size-triennial-review-of-the-national-nanotechnology, 2006.
"Heart Valve Materials—Bovine (cow)." Equine & Porcine Pericardium, Maverick Biosciences Pty. Lt, http://maverickbio.com/biological-medical-device-materials.php?htm. 2009.
"Pericardial Heart Valves." Edwards Lifesciences, Cardiovascular Surgery FAQ, http://www.edwards.com/products/cardiovascularsurgeryfaq.htm, Nov. 14, 2010.
Allen et al., "What are the characteristics of the ideal endovascular graft for abdominal aortic aneurysm exclusion?" J. Endovasc. Surg., 4(2):195-202 (May 1997).
Andersen et al. "Transluminal catheter implantation of a new expandable artificial cardiac valve (the stent-valve) in the aorta and the beating heart of closed chest pigs (Abstract)." Eur. Heart J., 11 (Suppl.): 224a (1990).
Andersen et al., "Transluminal implantation of artificial heart valves. Description of a new expandable aortic valve and initial results with implantation by catheter technique in closed chest pigs." Euro. Heart J., 13:704-708, May 1992.
Atwood et al., "Insertion of Heart Valves by Catheterization." Project Supervised by Prof. S. Muftu of Northeastern University 2001-2002: 36-40, May 30, 2002.
Atwood et al., "Insertion of Heart Valves by Catheterization." The Capstone Design Course Report. MIME 1501-1502. Technical Design Report. Northeastern University, pp. 1-93, Nov. 5, 2007.
Bailey, "Percutaneous Expandable Prosthetic Valves, Textbook of Interventional Cardiology." vol. 2, 2d ed. Eric J. Topol, W.B. Saunders Co. (1994).
Blum et al., "Endoluminal Stent-Grafts for Intrarenal Abdominal Aortic Aneurysms." New Engl. J. Med., 336:13-20 (1997).
Bodnar et al., "Replacement Cardiac Valves R Chapter 13: Extinct Cardiac Valve Prostheses." Pergamon Publishing Corporation. New York, 307-322, 1991.
Bonhoeffer et al., "Percutaneous Insertion of the Pulmonary Valve." J. Am. Coll. Cardiol., 39:1664-9 (2002).
Bonhoeffer et al., "Transcatheter Implantation of a Bovine Valve in Pulmonary Position: A Lamb Study." Circulation, 102: 813-16 (2000).
Bonhoeffer, et al., "Percutaneous replacement of pulmonary valve in a right ventricle to pulmonary-artery prosthetic conduit with valve dysfunction." The Lancet, vol. 356, 1403-05 (Oct. 21, 2000).
Boudjemline et al., "Percutaneous Implantation of a Biological Valve in the Aorta to Treat Aortic Valve Insufficiency—A Sheep Study." Med Sci. Monit., vol. 8, No. 4: BR113-116, Apr. 12, 2002.
Boudjemline et al., "Percutaneous Implantation of a Valve in the Descending Aorta in Lambs." Euro. Heart J., 23: 1045-1049, Jul. 2002.
Boudjemline et al., "Percutaneous Pulmonary Valve Replacement in a Large Right Ventricular Outflow Tract: An Experimental Study." Journal of the American College of Cardiology, vol. 43(6): 1082-1087, Mar. 17, 2004.
Boudjemline et al., "Percutaneous Valve Insertion: A New Approach?" J. of Thoracic and Cardio. Surg, 125(3): 741-743, Mar. 2003.
Boudjemline et al., "Steps Toward Percutaneous Aortic Valve Replacement." Circulation, 105: 775-778, Feb. 12, 2002.
Couper, "Surgical Aspects of Prosthetic Valve Selection," Overview of Cardiac Surgery for the Cardiologist, Springer-Verlag New York, Inc., 131-145 (1994).
Cribier et al., "Early Experience with Percutaneous Transcatheter Implantation of Heart Valve Prosthesis for the Treatment of End-Stage Inoperable Patients with Calcific Aortic Stenosis." J. of Am. Coll. of Cardio, 43(4): 698-703, Feb. 18, 2004.
Cribier et al., "Percutaneous Transcatheter Implantation of an Aortic Valve Prosthesis for Calcific Aortic Stenosis: First Human Case." Percutaneous Valve Technologies, Inc., 16 pages, Apr. 16, 2002.
Cribier et al., "Percutaneous Transcatheter Implementation of an Aortic Valve Prosthesis for Calcific Aortic Stenosis: First Human Case Description." Circulation, 106: 3006-3008, Dec. 10, 2002.
Cribier et al., "Trans-Cathether Implantation of Balloon-Expandable Prosthetic Heart Valves: Early Results in an Animal Model." Circulation [suppl. II] 104(17) II-552 (Oct. 23, 2001).
Cunanan et al., "Tissue Characterization and Calcification Potential of Commercial Bioprosthetic Heart Valves." Ann. Thorac. Surg., S417-421, May 15, 2001.
Cunliffe et al., "Glutaraldehyde Inactivation of Exotic Animal Viruses in Swine Heart Tissue." Applied and Environmental Microbiology, Greenport, New York, 37(5): 1044-1046, May 1979.
Dake et al., "Transluminal Placement of Endovascular Stent-Grafts for the Treatment of Descending Thoracic Aortic Aneurysms." New Engl. J. of Med., 331(26):1729-34 (1994).
Dalby et al., "Non-Surgical Aortic Valve Replacement" Br. J. Cardiol., 10:450-2 (2003).
Dhasmana, et al., "Factors Associated With Periprosthetic Leakage Following Primary Mitral Valve Replacement: With Special Consideration of Suture Technique." Annals of Thorac. Surg. 35(2), 170-8 (Feb. 1983).
Diethrich, AAA Stent Grafts: Current Developments, J. Invasive Cardiol. 13(5) (2001).
Dolmatch et al., Stent Grafts: Current Clinical Practice (2000)—EVT Endograft and Talent Endoprosthesis.
Dotter, "Transluminally-Placed Coilspring Endarterial Tube Grafts," Investigative Radiology, pp. 329-332 (1969).
Emery et al., "Replacement of the Aortic Valve in Patients Under 50 Years of Age: Long-Term Follow-Up of the St. Jude Medical Prosthesis." Ann. Thorac. Surg., 75:1815-9 (2003).
EP Search Report for EP Application No. 06824992.9, mailed Aug. 10, 2011.
Examiner's First Report on AU Patent Application No. 2011202667, issued on May 17, 2012.
Ferrari et al., "Percutaneous Transvascular Aortic Valve Replacement with Self-Expanding Stent-Valve Device." Poster from the presentation given at SMIT 2000, 12th International Conference. Sep. 5, 2000.
Greenberg, "Abdominal Aortic Endografting: Fixation and Sealing." J. Am. Coll. Surg. 194:1:S79-S87 (2002).
Grossi, "Impact of Minimally Invasive Valvular Heart Surgery: A Case-Control Study." Ann. Thorac. Surg., 71:807-10 (2001).
Helmus, "Mechanical and Bioprosthetic Heart Valves in Biomaterials for Artificial Organs." Woodhead Publishing Limited: 114-162, 2011.

(56) References Cited

OTHER PUBLICATIONS

Hijazi, "Transcatheter Valve Replacement: A New Era of Percutaneous Cardiac Intervention Begins." J. of Am. College of Cardio., 43(6): 1088-1089, Mar. 17, 2004.
Hourihan et al., "Transcatheter Umbrella Closure of Valvular and Paravalvular Leaks." JACC, Boston, Massachusetts, 20(6): 1371-1377, Nov. 15, 1992.
Huber et al., "Do Valved Stents Compromise Coronary Flow?" European Journal of Cardio-thoracic Surgery, vol. 25: 754-759, Jan. 23, 2004.
Ing, "Stents: What's Available to the Pediatric Interventional Cardiologist?" Catheterization and Cardiovascular Interventions 57:274-386 (2002).
Ionescu, et al., "Prevalence and Clinical Significance of Incidental Paraprosthetic Valvar Regurgitation: A prospective study using transesophageal echocardiography." Heart, 89:1316-21 (2003).
Kaiser, et al., "Surgery for Left Ventricle Outflow Obstruction: Aortic Valve Replacement and Myomectomy," Overview of Cardiac Surgery for the Cardiologist. Springer-Verlag New York, Inc., 40-45 (1994).
Kato et al., "Traumatic Thoracic Aortic Aneurysm: Treatment with Endovascular Stent-Grafts." Radiol., 205: 657-662 (1997).
Khonsari et al., "Cardiac Surgery: Safeguards and Pitfalls in Operative Technique." 3d ed., 45-74 (2003).
Carpentier-Edwards Perimount Bioprosthesis (2003).
International Search Report and Written Opinion dated Oct. 22, 2018 for International Application No. PCT/US2018/044318.
Knudsen et al., "Catheter-implanted prosthetic heart valves." Int'l J. of Art. Organs, 16(5): 253-262, May 1993.
Kort et al., "Minimally Invasive Aortic Valve Replacement: Echocardiographic and Clinical Results." Am. Heart J., 142(3): 476-481, Sep. 2001.
Lawrence et al., "Percutaneous Endovascular Graft: Experimental Evaluation," Radiology, 163(2): 357-60 (May 1987).
Levi et al., "Future of Interventional Cardiology in Pediactrics." Current Opinion in Cardiol., 18:79-90 (2003).
Levy, "Mycobacterium Chelonei Infection of Porcine Heart Valves." The New England Journal of Medicine, Washington DC, 297(12), Sep. 22, 1977.
Love et al., The Autogenous Tissue Heart Valve: Current Status. Journal of Cardiac Surgery, 6(4): 499-507, Mar. 1991.
Lutter et al., "Percutaneous Aortic Valve Replacement: An Experimental Study. I. Studies on Implantation." J. of Thoracic and Cardio. Surg., 123(4): 768-776, Apr. 2002.
Magovern et al., "Twenty-five-Year Review of the Magovern-Cromie Sutureless Aortic Valve." Ann. Thorac. Surg., 48: S33-4 (1989).
Maraj et al., Evaluation of Hemolysis in Patients with Prosthetic Heart Valves, Clin. Cardiol. 21, 387-392 (1998).
Mckay et al., "The Mansfield Scientific Aortic Valvuloplasty Registry: Overview of Acute Hemodynamic Results and Procedural Complications." J. Am. Coll. Cardiol. 17(2): 485-91 (Feb. 1991).
Mirich et al., "Percutaneously Placed Endovascular Grafts for Aortic Aneurysms: Feasibility Study." Radiology, 170: 1033-1037 (1989).
Moazami et al., "Transluminal Aortic Valve Placement: A Feasibility Study With a Newly Designed Collapsiable Aortic Valve," ASAIO J. vol. 42:5, pp. M383-85 (Sep./Oct. 1996).
Moulopoulos et al., "Catheter-Mounted Aortic Valves." Annals of Thoracic Surg., 11(5): 423-430, May 1971.
Paniagua et al., "Heart Watch." Texas Heart Institute. Edition: 8 pages, Spring, 2004.
Paniagua et al., "Percutaneous Heart Valve in the Chronic in Vitro Testing Model." Circulation, 106: e51-e52, Sep. 17, 2002.
Parodi et al., "Transfemoral Intraluminal Graft Implantation for Abdominal Aortic Aneurysms." Ann. Vasc. Surg., 5(6):491-9 (1991).
Pavcnik et al., "Percutaneous Bioprosthetic Venous Valve: A Long-term Study in Sheep." J. of Vascular Surg., 35(3): 598-603, Mar. 2002.
Pavcnik et al., "Development and Initial Experimental Evaluation of a Prosthetic Aortic Valve for Transcatheter Placement." Radiology 183:151-54 (1992).
Pavcnik, et al., "Aortic and venous valve for percutaneous insertion," Min. Invas. Ther. & Allied Technol. 9(3/4) 287-292 (2000).
Phillips et al., "A Temporary Catheter-Tip Aortic Valve: Hemodynamic Effects on Experimental Acute Aortic Insufficiency." Annals of Thoracic Surg., 21(2): 134-136, Feb. 1976.
Printz, et al., "Let the Blood Circulate." Sulzer Tech. Rev. 4/99.
U.S. Appl. No. 60/553,945 to White.
Raillat et al., "Treatment of Iliac Artery Stenosis with the Wallstent Endoprosthesis." AJR 154(3):613-6 (Mar. 1990).
Remadi et al., "Preliminary results of 130 aortic valve replacements with a new mechanical bileaflet prosthesis: the Edwards MIRA valve" Interactive Cardiovasc. and Thorac. Surg. 2, 80-83 (2003).
Rosch et al., "Gianturco-Rosch Expandable Z-Stents in the Treatment of Superior Vena Cava Syndrome." Cardiovasc. Intervent. Radiol. 15: 319-327 (1992).
Schurink et al,. "Stent Attachment Site-related Endoleakage after Stent Graft Treatment: An in vitro study of the effects of graft size, stent type, and atherosclerotic wall changes." J. Vasc. Surg., 30(4):658-67 (Oct. 1999).
Seminars in Interventional Cardiology, ed. P.W. Surruys, vol. 5 (2000).
Sochman et al., "Percutaneous Transcatheter Aortic Disc Valve Prosthesis Implantation: A Feasibility Study." Cardiovasc. Intervent. Radiol., 23: 384-388, Sep. 2000.
Southern Lights Biomaterials Homepage, http://www.slv.co.nz/, Jan. 7, 2011.
Stanley et al., "Evaluation of Patient Selection Guidelines for Endoluminal AAA Repair With the Zenith Stent Graft: The Australasian Experience." J. Endovasc. Ther. 8:457-464 (2001).
Thompson et al., "Endoluminal stent grafting of the thoracic aorta: Initial experience with the Gore Excluder," Journal of Vascular Surgery, 1163-70 (Jun. 2002).
Steinhoff et al., "Tissue Engineering of Pulmonary Heart Valves on Allogenic Acellular Matrix Conduits." Circulation, 102 [suppl. III]: III-50-III-55 (2000).
Stuart, "In Heart Valves, A Brave, New Non-Surgical World." Start-Up. 9-17, Feb. 2004.
Supplemental Search Report from EP Patent Office, EP Application No. 04815634.3, Aug. 19, 2011.
Supplemental Search Report from EP Patent Office, EP Application No. 05758878.2, Oct. 24, 2011.
Topol, Textbook of Interventional Cardiology, 2d Ed., Chapter 75: Percutaneous Expandable Prosthetic Valves (1994).
Stassano, "Mid-term Results of the Valve on Valve Technique for Bioprosthetic failure." European journal of Ccardiothoracic Surgery:vol. 18, 453-457, Oct. 2000.
Topol, "Percutaneous Expandable Prosthetic Valves." Textbook of Interventional Cardiology, W.B. Saunders Company, 2: 1268-1276, 1994.
Vahanian et al., "Percutaneous Approaches to Valvular Disease." Circulation, 109: 1572-1579, Apr. 6, 2004.
Van Herwerden et al., "Percutaneous Valve Implantation: Back to the Future?" Euro. Heart J., 23(18): 1415-1416, Sep. 2002.
VentureBeatProfiles, Claudio Argento, Jan. 7, 2010, http://venturebeatprofiles.com/person/profile/claudio-argento.
Vossoughi et al., Stent Graft Update (2000)—Kononov, Volodos, and Parodi and Palmaz Stents; Hemobahn Stent Graft.
White et al., "Endoleak as a Complication of Endoluminal Grafting of Abdominal Aortic Aneurysms: Classification, Incidence, Diagnosis, and Management." J. Endovac. Surg., 4:152-168 (1997).
Yoshioka et al., "Self-Expanding Endovascular Graft: An Experimental Study in Dogs." AJR 151: 673-76 (Oct. 1988).
USPTO Case IPR2017-01293, U.S. Pat. No. 8,992,608 B, Oct. 13, 2017.
Zhou et al., "Self-expandable Valved Stent of Large Size: Off-Bypass Implantation in Pulmonary Position." Eur. J. Cardiothorac, 24: 212-216, Aug. 2003.
Gore Excluder Instructions for Use (2002).
USPTO Case IPR2016-_____, U.S. Pat. No. 8,992,608 "Petition for Interpartes Review of U.S. Pat. No. 8,992,608" Oct. 12, 2016.

(56) References Cited

OTHER PUBLICATIONS

USPTO Case IPR 2017-0006, U.S. Pat. No. 8,992,608 B2, "Final Written Decision" Mar. 23, 2018.
Fluency Vascular Stent Graft Instructions for Use (2003).

* cited by examiner

REPLACEMENT HEART VALVE SYSTEM

CROSS-REFERENCE TO RELATED APPLICATIONS

This application claims the benefit of priority of U.S. Provisional Application No. 63/451,255 filed Mar. 10, 2023, the entire disclosure of which is hereby incorporated by reference.

TECHNICAL FIELD

The disclosure relates generally to medical devices and more particularly to medical devices that are adapted for implanting stents and medical devices including a stent component.

BACKGROUND

A wide variety of intracorporeal medical devices have been developed for medical use including, artificial heart valves for repair or replacement of diseased heart valves. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

In one example, a replacement heart valve system may comprise a replacement heart valve implant comprising an expandable framework configured to shift from a radially collapsed configuration to a radially expanded configuration, wherein the expandable framework is self-biased toward the radially expanded configuration, and a plurality of valve leaflets attached to the expandable framework. The replacement heart valve system may comprise an implant delivery system comprising a handle and an elongate shaft assembly, the elongate shaft assembly comprising a tubular member fixedly attached to the handle, and an implant holding portion configured to constrain the expandable framework in the radially collapsed configuration. The elongate shaft assembly further comprises an expandable balloon disposed on the tubular member within the implant holding portion, the expandable balloon being configured to shift between a deflated configuration and an inflated configuration. When the expandable framework is constrained within the implant holding portion in the radially collapsed configuration, at least a portion of the expandable framework extends distal of the expandable balloon in the deflated configuration.

In addition or alternatively to any example described herein, the expandable balloon includes a proximal tapered portion, a distal tapered portion, and a body portion extending from the proximal tapered portion to the distal tapered portion.

In addition or alternatively to any example described herein, the expandable framework has a greater axial length than the body portion of the expandable balloon.

In addition or alternatively to any example described herein, the body portion has a constant outer diameter from the proximal tapered portion to the distal tapered portion.

In addition or alternatively to any example described herein, the tubular member includes an inflation lumen extending from an inflation port on the handle to the expandable balloon.

In addition or alternatively to any example described herein, the expandable balloon is non-compliant.

In addition or alternatively to any example described herein, the implant delivery system is configured to inflate the expandable balloon within the expandable framework to urge a portion of the expandable framework radially outward.

In addition or alternatively to any example described herein, a replacement heart valve system may comprise a replacement heart valve implant comprising an expandable framework configured to shift from a radially collapsed configuration to a radially expanded configuration, wherein the expandable framework is self-biased toward the radially expanded configuration and the expandable framework includes an anchoring portion extending from an inflow end to an outflow end, and a plurality of stabilization arches extending downstream from the outflow end, and a plurality of valve leaflets attached to the expandable framework. The replacement heart valve system may comprise an implant delivery system comprising a handle and an elongate shaft assembly, the elongate shaft assembly comprising a tubular member fixedly attached to the handle, and an implant holding portion configured to constrain the expandable framework in the radially collapsed configuration. The elongate shaft assembly further comprises an expandable balloon disposed on the tubular member within the implant holding portion, the expandable balloon including a proximal tapered portion, a distal tapered portion, and a body portion extending from the proximal tapered portion to the distal tapered portion, and wherein the expandable balloon is configured to shift between a deflated configuration and an inflated configuration. Upon release from the implant holding portion, the expandable framework is configured to shift toward the radially expanded configuration and the inflow end is offset longitudinally from the body portion of the expandable balloon in the deflated configuration and before shifting to the inflated configuration.

In addition or alternatively to any example described herein, the inflow end is offset distally from the body portion of the expandable balloon in the deflated configuration.

In addition or alternatively to any example described herein, the plurality of stabilization arches extends proximal of the body portion of the expandable balloon when the inflow end is offset distally from the body portion of the expandable balloon in the deflated configuration.

In addition or alternatively to any example described herein, the implant delivery system is configured to advance the expandable balloon distally relative to the expandable framework before shifting the expandable balloon from the deflated configuration to the inflated configuration.

In addition or alternatively to any example described herein, the implant delivery system is configured to center the body portion of the expandable balloon longitudinally within the expandable framework with respect to the inflow end and the outflow end before shifting the expandable balloon from the deflated configuration to the inflated configuration.

In addition or alternatively to any example described herein, the body portion of the expandable balloon is configured to urge the anchoring portion of the expandable framework radially outward when the expandable balloon is shifted from the deflated configuration to the inflated configuration.

In addition or alternatively to any example described herein, a method of delivering a replacement heart valve implant to a native heart valve may comprise: advancing an implant delivery system to a position adjacent the native heart valve, wherein an expandable framework of the replacement heart valve implant is constrained within an implant holding portion of the implant delivery system in a radially collapsed configuration, wherein the expandable framework is self-biased toward a radially expanded configuration; wherein the implant delivery system includes an expandable balloon disposed on a tubular member within the implant holding portion, the expandable balloon being configured to shift between a deflated configuration and an inflated configuration; wherein when the expandable framework is constrained within the implant holding portion in the radially collapsed configuration, at least a portion of the expandable framework extends distal of the expandable balloon in the deflated configuration; and releasing the expandable framework from the implant holding portion of the implant delivery system within the native heart valve such that the expandable framework is permitted to shift from the radially collapsed configuration to the radially expanded configuration.

In addition or alternatively to any example described herein, the method may further comprise translating the implant delivery system relative to the replacement heart valve implant to position the expandable balloon within the expandable framework such that at least a portion of the expandable balloon extends distal of the expandable framework; and shifting the expandable balloon to the inflated configuration within the expandable framework to urge a portion of the expandable framework radially outward.

In addition or alternatively to any example described herein, translating the implant delivery system relative to the replacement heart valve implant includes translating the expandable balloon distally relative to the expandable framework to longitudinally center a body portion of the expandable balloon with respect to the inflow end and the outflow end prior to shifting the expandable balloon to the inflated configuration.

In addition or alternatively to any example described herein, the implant delivery system includes at least one radiopaque marker correlated to the expandable balloon and configured to center the body portion of the expandable balloon with respect to the inflow end and the outflow end under fluoroscopy prior to shifting the expandable balloon to the inflated configuration.

In addition or alternatively to any example described herein, when the expandable framework is constrained within the implant holding portion in the radially collapsed configuration, at least a portion of the expandable framework extends proximal of the expandable balloon in the deflated configuration.

In addition or alternatively to any example described herein, the method further comprises: after releasing the expandable framework from the implant holding portion, assessing deployment of the replacement heart valve implant within the native heart valve for paravalvular leakage prior to withdrawing the implant delivery system from the position adjacent the native heart valve.

In addition or alternatively to any example described herein, the method, wherein if paravalvular leakage exceeds a predetermined value, further comprises: translating the implant delivery system relative to the replacement heart valve implant to position the expandable balloon within the expandable framework such that at least a portion of the expandable balloon extends distal of the expandable framework; and shifting the expandable balloon to the inflated configuration within the expandable framework to urge a portion of the expandable framework radially outward.

The above summary of some embodiments, aspects, and/or examples is not intended to describe each disclosed embodiment or every implementation of the present disclosure. The figures and detailed description which follow more particularly exemplify these embodiments.

BRIEF DESCRIPTION OF THE DRAWINGS

The disclosure may be more completely understood in consideration of the following detailed description in connection with the accompanying drawings, in which.

Figure 1:
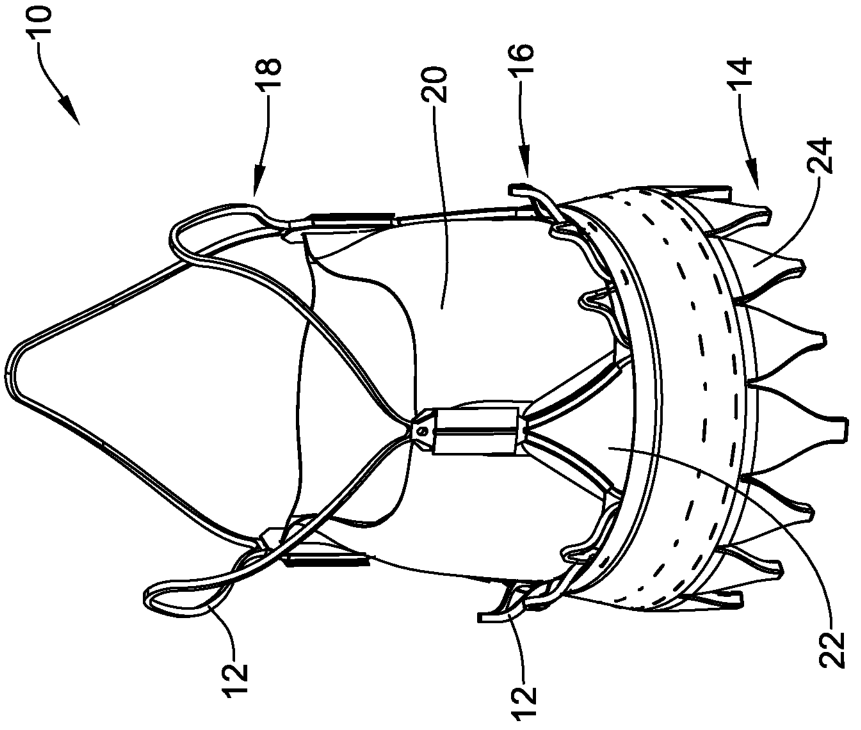
FIG. 1 illustrates selected aspects of a replacement heart valve implant.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the disclosure. Those skilled in the art will recognize that the various elements described and/or shown may be arranged in various combinations and configurations without departing from the scope of the disclosure. The detailed description and drawings illustrate example embodiments of the disclosure.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For example, a reference to one feature may be equally referred to all instances and quantities beyond one of said feature unless clearly stated to the contrary. As such, it will be understood that the following discussion may apply equally to any and/or all components for which there are more than one within the device, etc. unless explicitly stated to the contrary.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean the greatest measurement of a stated or identified dimension, unless the extent or dimension in question is preceded by or identified as a "minimum", which may be understood to mean the smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to implement the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Additionally, it should be noted that in any given figure, some features may not be shown, or may be shown schematically, for clarity and/or simplicity. Additional details regarding some components and/or method steps may be illustrated in other figures in greater detail. The devices and/or methods disclosed herein may provide a number of desirable features and benefits as described in more detail below.

FIG. 1 illustrates selected aspects of a replacement heart valve implant 10. It should be appreciated that the replacement heart valve implant 10 can be any type of replacement heart valve (e.g., a mitral valve, an aortic valve, etc.). In use, the replacement heart valve implant 10 may be implanted (e.g., surgically or through transcatheter delivery) in a mammalian heart. The replacement heart valve implant 10 can be configured to allow one-way flow through the replacement heart valve implant 10 from an inflow end to an outflow end.

For the purpose of this disclosure, the discussion herein is directed toward use in treating a native heart valve such as the aortic valve and will be so described in the interest of brevity. This, however, is not intended to be limiting as the skilled person will recognize that the following discussion may also apply to other heart valves, vessels, and/or treatment locations within a patient with no or minimal changes to the structure and/or scope of the disclosure.

The replacement heart valve implant 10 may include an expandable framework 12 defining a central lumen. In some embodiments, the expandable framework 12 may have a substantially circular cross-section. In some embodiments, the expandable framework 12 can have a non-circular (e.g., D-shaped, elliptical, etc.) cross-section. Some suitable but non-limiting examples of materials that may be used to form the expandable framework 12, including but not limited to metals and metal alloys, composites, ceramics, polymers, and the like, are described below. The expandable framework 12 may be configured to shift between a radially collapsed configuration and a radially expanded configuration. In some embodiments, the expandable framework 12 may be self-expanding from the radially collapsed configuration to the radially expanded configuration. In some embodiments, the expandable framework 12 may be self-biased toward the radially expanded configuration. In some alternative embodiments, the expandable framework 12 may be mechanically expandable from the radially collapsed configuration to the radially expanded configuration. In some alternative embodiments, the expandable framework 12 may be balloon expandable from the radially collapsed configuration to the radially expanded configuration. Other configurations are also contemplated. In some embodiments, the expandable framework 12 may include and/or define a plurality of interstices (e.g., openings) through the expandable framework 12.

In some embodiments, the expandable framework 12 may include and/or define a lower crown 14 proximate an inflow end, an upper crown 16 proximate an outflow end, and a plurality of stabilization arches 18 extending downstream from the outflow end. In some embodiments, the lower crown 14 may be disposed at the inflow end. In some embodiments, the upper crown 16 may be disposed at the outflow end. In some embodiments, the expandable framework 12 may include a tubular wall defining the central lumen, the inflow end, the outflow end, the lower crown 14, and/or the upper crown 16.

In some embodiments, the expandable framework 12 may include an anchoring portion extending from the inflow end to the outflow end. In some embodiments, the anchoring portion may include the lower crown 14 and the upper crown 16. In some embodiments, the anchoring portion may extend from the lower crown 14 to the upper crown 16. In some embodiments, the anchoring portion may include the tubular wall. In some embodiments, the tubular wall may define the anchoring portion.

In some embodiments, the expandable framework 12 may include and/or define a plurality of commissure posts proximate the outflow end. In some embodiments, the plurality of commissure posts may at least partially define the outflow end. Other configurations are also contemplated. In some embodiments, the plurality of commissure posts may be disposed longitudinally and/or axially between the upper crown 16 and the plurality of stabilization arches 18. In some embodiments, the plurality of stabilization arches 18 may extend downstream of and/or away from the upper crown 16 and/or the plurality of commissure posts in a direction opposite the lower crown 14. In some embodiments, the upper crown 16 may be disposed longitudinally and/or axially between the lower crown 14 and the plurality of stabilization arches 18. In some embodiments, the upper crown 16 may be disposed longitudinally and/or axially between the lower crown 14 and the plurality of commissure posts.

In some embodiments, the replacement heart valve implant 10 may include a proximal portion and a distal portion. In some embodiments, orientation of the replacement heart valve implant 10 may be related to an implant delivery device and/or a direction of implantation relative to a target site. In some embodiments, the proximal portion may include the outflow end and/or the plurality of stabilization arches 18. In some embodiments, the proximal portion may include the plurality of commissure posts, the upper crown 16, and/or the plurality of valve leaflets 20. In some embodiments, the distal portion may include the inflow end and/or the lower crown 14. Other configurations are also contemplated.

In some embodiments, the replacement heart valve implant 10 may include a plurality of valve leaflets 20 disposed within the central lumen. The plurality of valve leaflets 20 may be coupled, secured, and/or fixedly attached to the expandable framework 12. In at least some embodiments, the plurality of valve leaflets 20 may be coupled, secured, and/or fixedly attached to the expandable framework 12 at the plurality of commissure posts to form and/or define a plurality of commissures.

Each of the plurality of valve leaflets 20 may include a root edge coupled to the expandable framework 12 and a free edge (e.g., a coaptation edge) movable relative to the root edge to coapt with the free edges of the other valve leaflets along a coaptation region. In some embodiments, the plurality of valve leaflets 20 can be integrally formed with each other, such that the plurality of valve leaflets 20 is formed as a single unitary and/or monolithic unit. In some embodiments, the plurality of valve leaflets 20 may be formed integrally with other structures such as an inner skirt 22 and/or an outer skirt 24, base structures, liners, or the like.

The plurality of valve leaflets 20 may be configured to substantially restrict fluid from flowing through the replacement heart valve implant 10 in a closed position. For example, in some embodiments, the free edges of the plurality of valve leaflets 20 may move into coaptation with one another in the closed position to substantially restrict fluid from flowing through the replacement heart valve implant 10. The free edges of the plurality of valve leaflets 20 may be moved apart from each other in an open position to permit fluid flow through the replacement heart valve implant 10. In FIG. 1, the plurality of valve leaflets 20 is shown in the open position or in a partially open position (e.g., a neutral position) that the plurality of valve leaflets 20 may move to when unbiased by fluid flow.

In some embodiments, the plurality of valve leaflets 20 may be comprised of a polymer, such as a thermoplastic polymer. In some embodiments, the plurality of valve leaflets 20 may include at least 50 percent by weight of a polymer. In some embodiments, the plurality of valve leaflets 20 may be formed from bovine pericardial or other living tissue. Other configurations and/or materials are also contemplated.

In some embodiments, the replacement heart valve implant 10 may include an inner skirt 22 disposed on and/or extending along an inner surface of the expandable framework 12. In at least some embodiments, the inner skirt 22 may be fixedly attached to the expandable framework 12. The inner skirt 22 may direct fluid, such as blood, flowing through the replacement heart valve implant 10 toward the plurality of valve leaflets 20. In at least some embodiments, the inner skirt 22 may be fixedly attached to and/or integrally formed with the plurality of valve leaflets 20. The inner skirt 22 may ensure the fluid flows through the central lumen of the replacement heart valve implant 10 and does not flow around the plurality of valve leaflets 20 when they are in the closed position.

In some embodiments, the replacement heart valve implant 10 can include an outer skirt 24 disposed on and/or extending along an outer surface of the expandable framework 12. In some embodiments, the outer skirt 24 may be disposed at and/or adjacent the lower crown 14. In some embodiments, the outer skirt 24 may be disposed between the expandable framework 12 and the vessel wall in order to prevent fluid, such as blood, flowing around the replacement heart valve implant 10 and/or the expandable framework 12 in a downstream direction. The outer skirt 24 may ensure the fluid flows through the replacement heart valve implant 10 and does not flow around the replacement heart valve implant 10, so as to ensure that the plurality of valve leaflets 20 can stop the flow of fluid when in the closed position.

In some embodiments, the inner skirt 22 may include a polymer, such as a thermoplastic polymer. In some embodiments, the inner skirt 22 may include at least 50 percent by weight of a polymer. In some embodiments, the outer skirt 24 may include a polymer, such as a thermoplastic polymer. In some embodiments, the outer skirt 24 may include at least 50 percent by weight of a polymer. In some embodiments, one or more of the plurality of valve leaflets 20, the inner skirt 22, and/or the outer skirt 24 may be formed of the same polymer or polymers. In some embodiments, the polymer may be a polyurethane. In some embodiments, the inner skirt 22 and/or the outer skirt 24 may be substantially impervious to fluid. In some embodiments, the inner skirt 22 and/or the outer skirt 24 may be formed from a thin tissue (e.g., bovine pericardial, etc.). In some embodiments, the inner skirt 22 and/or the outer skirt 24 may be formed from a coated fabric material. In some embodiments, the inner skirt 22 and/or the outer skirt 24 may be formed from a nonporous and/or impermeable fabric material. Other configurations are also contemplated. Some suitable but non-limiting examples of materials that may be used to form the inner skirt 22 and/or the outer skirt 24 including but not limited to polymers, composites, and the like, are described below.

In some embodiments, the inner skirt 22 and/or the outer skirt 24 may seal one of, some of, a plurality of, or each of the plurality of interstices formed in the expandable framework 12. In at least some embodiments, sealing the interstices may be considered to prevent fluid from flowing through the interstices of the expandable framework 12. In some embodiments, the inner skirt 22 and/or the outer skirt 24 may be attached to the expandable framework 12 and/or the plurality of frame struts using one or more methods including but not limited to tying with sutures or filaments, adhesive bonding, melt bonding, embedding or over molding, welding, etc.

In some embodiments, the replacement heart valve implant 10 may include a sealing member disposed on the expandable framework 12 proximate the inflow end. In some embodiments, the sealing member may include and/or may be the inner skirt 22. In some embodiments, the sealing member may include and/or may be the outer skirt 24. In some embodiments, the sealing member may include and/or may be the inner skirt 22 and the outer skirt 24. Other configurations are also contemplated.

In some embodiments, the expandable framework 12 and/or the replacement heart valve implant 10 may have an outer extent of about 23 millimeters (mm), about 25 mm, about 27 mm, about 30 mm, etc. in an unconstrained configuration (e.g., in the radially expanded configuration). In some embodiments, the expandable framework 12 and/or the replacement heart valve implant 10 may have an outer extent of about 10 mm, about 9 mm about 8 mm, about 7 mm, about 6 mm, etc. in the radially collapsed configuration. Other configurations are also contemplated.

Figure 2:
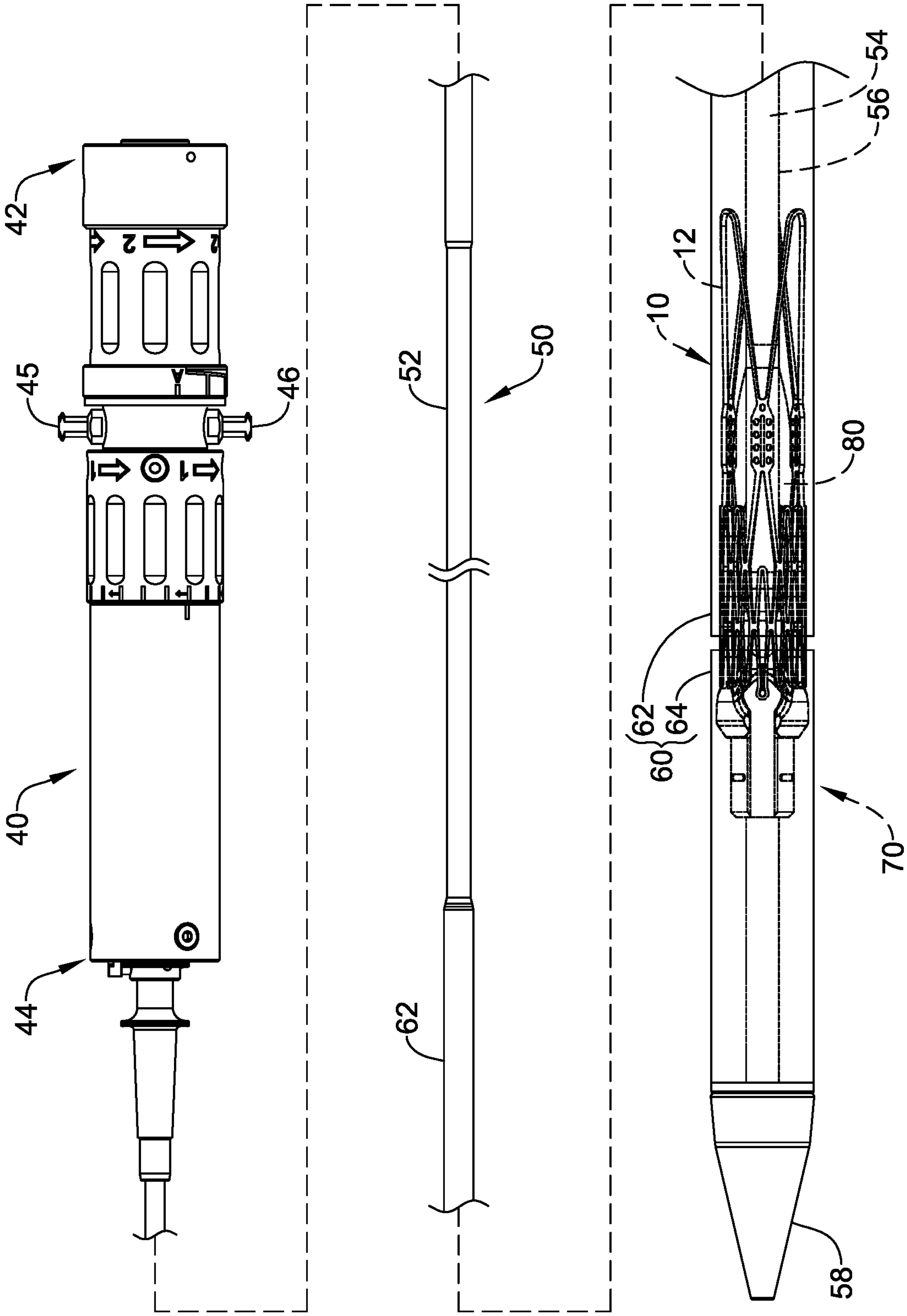
FIGS. 2-4 illustrate selected aspects of a replacement heart valve system.
Figure 3:
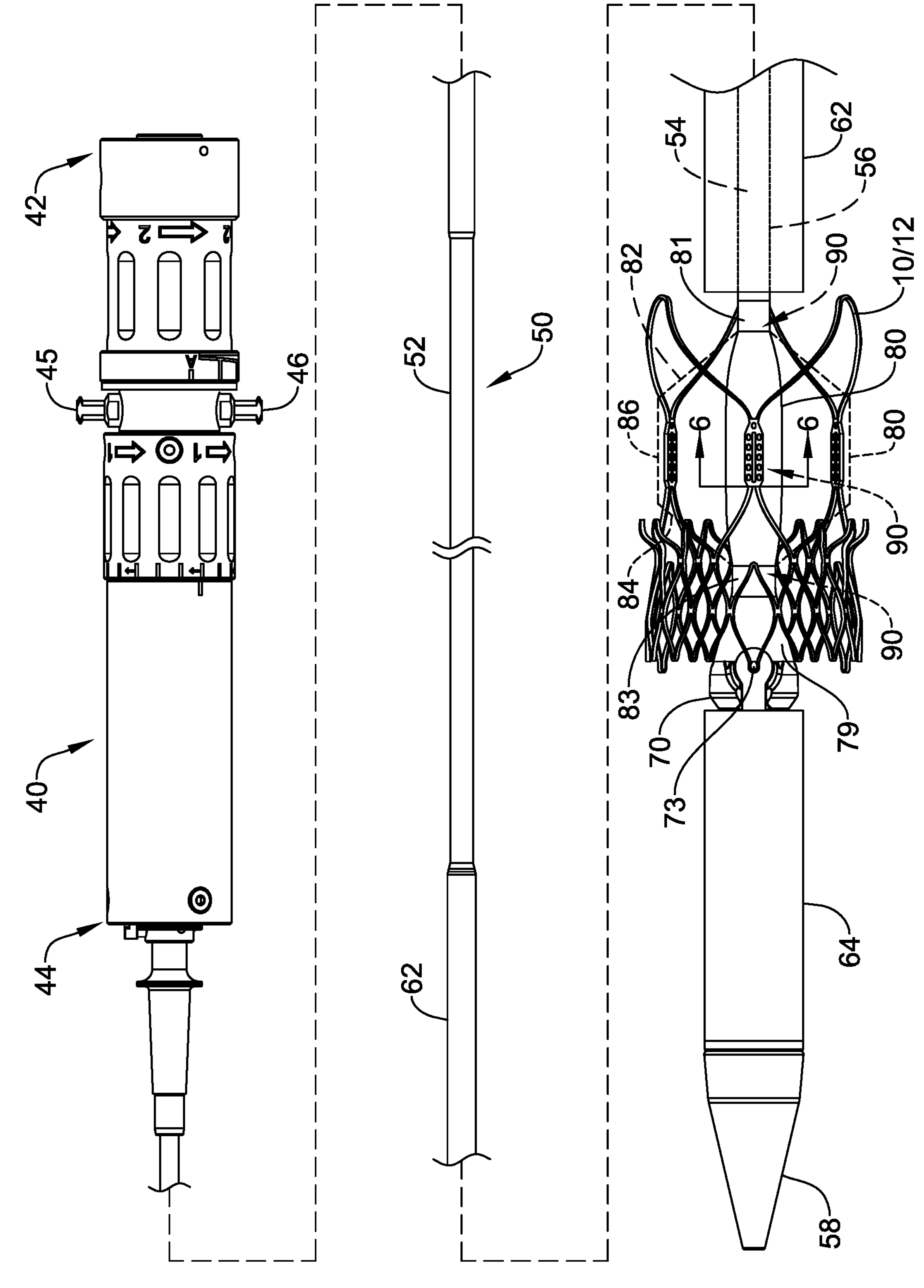
Figure 4:
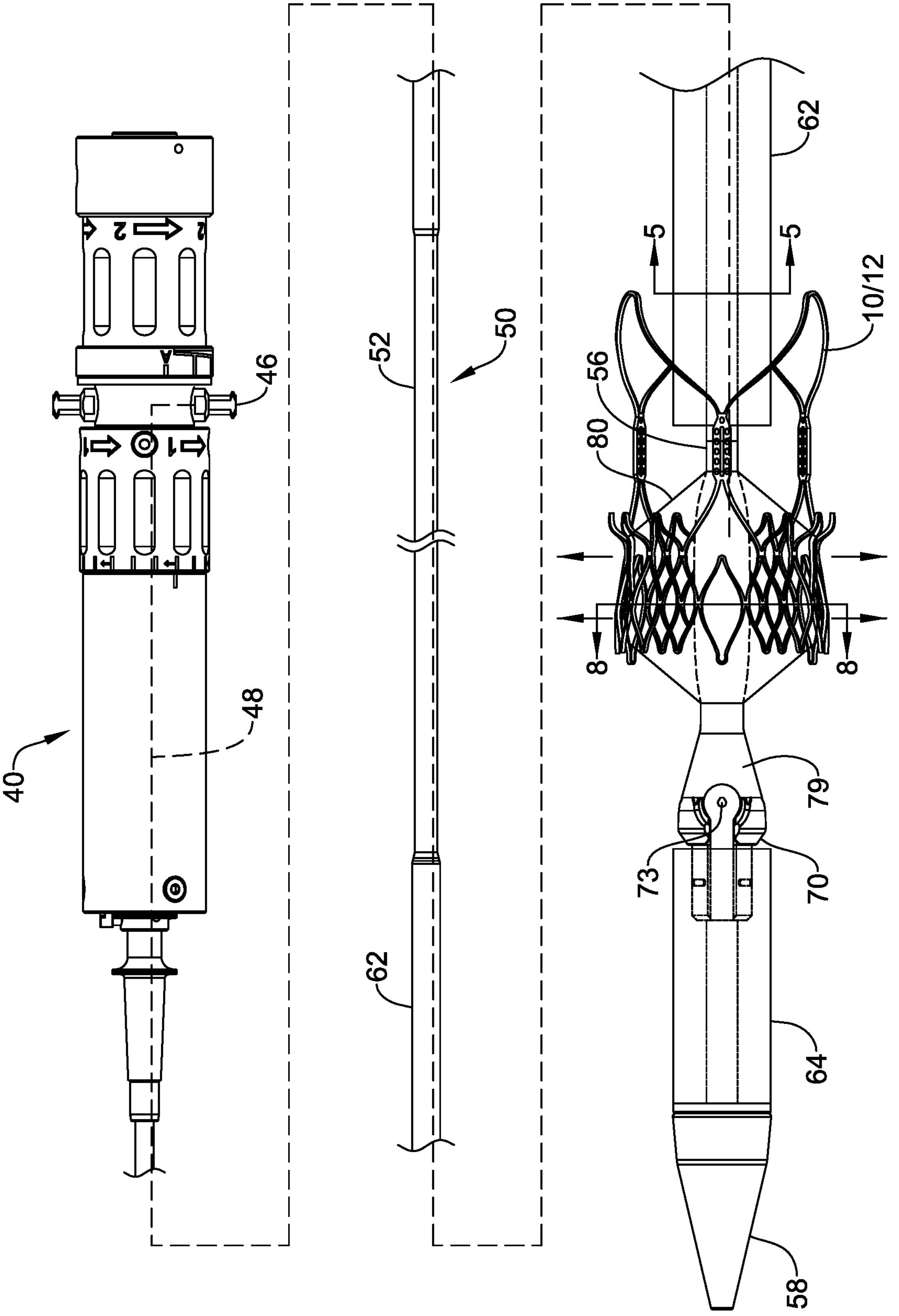

FIG. 2-4 illustrate selected aspects of a replacement heart valve system including the replacement heart valve implant 10 and an implant delivery system 30 for delivering a replacement heart valve implant to a native heart valve (e.g., the aortic valve). The implant delivery system 30 may be compatible with and/or usable with the replacement heart valve implant 10. In FIG. 2, some elements that would be hidden from view are shown in phantom to show relative positioning. In FIGS. 2-4, only the expandable framework 12 of the replacement heart valve implant 10 is shown. Other elements of the replacement heart valve implant 10 have been omitted to improve clarity. It should also be noted that FIGS. 2-4 include at least one change of scale (e.g., all parts of the figure are not drawn to the same scale) to improve viewability and show additional detail of selected aspects of the implant delivery system 30.

The implant delivery system 30 may include a handle 40 and an elongate shaft assembly 50 extending distally from the handle 40. The handle 40 may include a first end 42 and a second end 44 opposite the first end 42. The elongate shaft assembly 50 may extend distally from the second end 44 of the handle 40. The handle 40 may include a flush port 45 in fluid communication with at least a portion of the elongate shaft assembly 50. The handle 40 may include an inflation port 46, which will be discussed in more detail herein. The handle 40 may include one or more rotatable knobs. In some embodiments, the one or more rotatable knobs may include a first rotatable knob and a second rotatable knob. In at least some embodiments, the first rotatable knob and/or the second rotatable knob may be configured to rotate about a central longitudinal axis of the implant delivery system 30 and/or the handle 40.

In some embodiments, a distal portion of the implant delivery system 30 and/or the elongate shaft assembly 50 may include an implant holding portion 60 configured to engage with and/or constrain the replacement heart valve implant 10 and/or the expandable framework 12 in the radially collapsed configuration, as seen in FIG. 2. The elongate shaft assembly 50 may comprise a tubular member fixedly attached to the handle 40.

In some embodiments, the elongate shaft assembly 50 may include an outer tubular member 52 extending distally from the handle 40 and an inner shaft 54 extending distally from the handle 40 within the outer tubular member 52 to a distal tip 58 disposed distal of the implant holding portion 60. In some embodiments, the implant holding portion 60 may comprise a proximal sheath 62 and a distal sheath 64. In some embodiments, the proximal sheath 62 and/or the distal sheath 64 may be formed from a polymeric material. In some embodiments, the proximal sheath 62 and/or the distal sheath 64 may include a reinforcing structure disposed therein and/or thereon. In some embodiments, the reinforcing structure may be a coil, a mesh, one or more filaments, bands, or strips, or another suitable structure. Other configurations are also contemplated.

In some embodiments, the inner shaft 54 may be slidably disposed within a lumen of the outer tubular member 52. In some embodiments, the elongate shaft assembly 50 and/or the tubular member fixedly attached to the handle 40 may include an intermediate tubular member 56 disposed within and/or radially inward of the outer tubular member 52 and about and/or radially outward of the inner shaft 54. In some embodiments, the inner shaft 54 may be slidably disposed within a lumen of the tubular member and/or the intermediate tubular member 56. In at least some embodiments, the inner shaft 54 and the outer tubular member 52 are each axially translatable relative to the intermediate tubular member 56 independently of each other. For example, the inner shaft 54 may be translated relative to the intermediate tubular member 56 without translating the outer tubular member 52 relative to the intermediate tubular member 56, and vice versa.

In some embodiments, the proximal sheath 62 may be fixedly attached to the outer tubular member 52. In some embodiments, the proximal sheath 62 may be fixedly attached to and/or may extend distally from a distal end of the outer tubular member 52. In some embodiments, the distal sheath 64 and/or the distal tip 58 may be fixedly attached to the inner shaft 54. In some embodiments, the distal sheath 64 may be fixedly attached to the distal tip 58. In some embodiments, the distal sheath 64 may extend proximally from the distal tip 58. In some embodiments, the inner shaft 54 may include and/or at least partially define a guidewire lumen extending therethrough. In some embodiments, the guidewire lumen may extend through the handle 40.

In some embodiments, the handle 40 may be configured to manipulate and/or translate the proximal sheath 62 and/or the distal sheath 64 relative to each other using the first rotatable knob and/or the second rotatable knob. In some embodiments, the handle 40 may be configured to manipulate and/or translate the inner shaft 54 and/or the distal sheath 64 relative to the elongate shaft assembly 50, the outer tubular member 52, the intermediate tubular member 56, and/or the proximal sheath 62. In some embodiments, the handle 40 may be configured to manipulate and/or translate the outer tubular member 52 and/or the proximal sheath 62 relative to the elongate shaft assembly 50, the inner shaft 54, the intermediate tubular member 56, and/or the distal sheath 64.

During delivery of the replacement heart valve implant 10 to a treatment site (e.g., the native heart valve, the aortic valve, etc.), the replacement heart valve implant 10 and/or the expandable framework 12 may be disposed at least partially within the proximal sheath 62 and/or the distal sheath 64 in the radially collapsed configuration in a closed configuration of the implant holding portion 60 (e.g., FIG. 2). In some embodiments, the proximal sheath 62 and/or the distal sheath 64 may collectively define the implant holding portion 60 of the implant delivery system 30. In some embodiments, the implant holding portion 60 may be configured to constrain the replacement heart valve implant 10 and/or the expandable framework 12 in the radially collapsed configuration when the implant holding portion 60 is in the closed configuration (e.g., FIG. 2). In some embodiments, the replacement heart valve implant 10 and/or the expandable framework 12 may be releasably coupled to the inner shaft 54, the intermediate tubular member 56, and/or a stent holder 70 (described in more detail below) when the replacement heart valve implant 10 and/or the expandable framework 12 is constrained within the implant holding portion 60 of the implant delivery system 30 in the radially collapsed configuration.

In some embodiments, the proximal sheath 62 may be configured to cover the proximal portion and/or the outflow end of the replacement heart valve implant 10 and/or the expandable framework 12 in the radially collapsed configuration when the implant holding portion 60 is in the closed configuration, and the distal sheath 64 may be configured to cover the distal portion and/or the inflow end of the replacement heart valve implant 10 and/or the expandable framework 12 in the radially collapsed configuration when the implant holding portion 60 is in the closed configuration. In some embodiments, the proximal sheath 62 may be disposed adjacent to the distal sheath 64 in the closed configuration. In some embodiments, the proximal sheath 62 may abut the distal sheath 64 in the closed configuration. In some embodiments, the proximal sheath 62 may be axially spaced apart from the distal sheath 64 in the closed configuration. In some embodiments, the proximal sheath 62 may be axially spaced apart from the distal sheath 64 in the closed configuration by less than 20% of an overall length of the replacement heart valve implant 10 and/or the expandable framework 12. In some embodiments, the proximal sheath 62 may be axially spaced apart from the distal sheath 64 in the closed configuration by less than 15% of an overall length of the replacement heart valve implant 10 and/or the expandable framework 12. In some embodiments, the proximal sheath 62 may be axially spaced apart from the distal sheath 64 in the closed configuration by less than 10% of an overall length of the replacement heart valve implant 10 and/or the expandable framework 12. In some embodiments, the proximal sheath 62 may be axially spaced apart from the distal sheath 64 in the closed configuration by less than 5% of an overall length of the replacement heart valve implant 10 and/or the expandable framework 12. Other configurations are also contemplated.

After advancing the replacement heart valve system and/or the implant delivery system 30 to a position adjacent the native heart valve (e.g., the aortic valve), the replacement heart valve implant 10 and/or the expandable framework 12 may be deployed within the native heart valve (e.g., the aortic valve). Deploying the replacement heart valve implant 10 and/or the expandable framework 12 may include shifting the proximal sheath 62 and the distal sheath 64 of the implant holding portion 60 from the closed configuration to an open configuration, as seen in FIG. 3. In some embodiments, shifting the proximal sheath 62 and the distal sheath 64 of the implant holding portion 60 from the closed configuration to the open configuration may include shifting the proximal sheath 62 and the distal sheath 64 of the implant holding portion 60 axially apart from each other.

In some embodiments, the implant holding portion 60 and/or the elongate shaft assembly 50 may include the stent holder 70, seen in FIGS. 3-4. In at least some embodiments, the stent holder 70 may be fixedly attached to the elongate shaft assembly 50. In some embodiments, the stent holder 70 may be fixedly attached to the intermediate tubular member 56 of the elongate shaft assembly 50. In some embodiments, the stent holder 70 may be integrally formed with the elongate shaft assembly 50 and/or the intermediate tubular member 56. In some embodiments, the stent holder 70 may be configured to engage the expandable framework 12 in the radially collapsed configuration and/or when the replacement heart valve implant 10 is constrained within the implant holding portion 60 of the implant delivery system 30. In some embodiments, the stent holder 70 may include at least one projection 73 configured to engage the expandable framework 12 in the radially collapsed configuration. In some embodiments, the at least one projection 73 may be configured to engage the inflow end of the expandable framework 12 in the radially collapsed configuration. In some embodiments, the at least one projection 73 may extend into and/or through interstices of the expandable framework 12. In some embodiments, the expandable framework 12 may include at least one mounting loop configured to receive and/or engage with the at least one projection 73. Other configurations are also contemplated.

The implant delivery system 30 and/or the elongate shaft assembly 50 may include a primary visual indicator (not shown) disposed within the replacement heart valve implant 10 when the replacement heart valve implant 10 and/or the expandable framework 12 is constrained within the implant holding portion 60 in the radially collapsed configuration. The primary visual indicator may be configured and/or adapted to be visible under fluoroscopy with an imaging device. Other imaging means suitable for use with transcatheter surgical procedures are also contemplated. The implant delivery system 30 and/or the primary visual indicator may be configured to cooperate with the imaging device to position the replacement heart valve implant 10 at a desired insertion depth within the native heart valve (e.g., the aortic valve). In some embodiments, the primary visual indicator may be fixedly attached to the elongate shaft assembly 50 and/or the intermediate tubular member 56 by a shrink wrap or by an adhesive element. In some embodiments, the primary visual indicator may be and/or may include a marker band. In some embodiments, the primary visual indicator may be at least partially radiopaque. In some embodiments, the primary visual indicator may be completely radiopaque. Other configurations are also contemplated.

In use, the implant delivery system 30 may be advanced to a position adjacent to the treatment site (e.g., the native heart valve). In one example, the implant delivery system 30 may be advanced through the vasculature and across the aortic arch to a position adjacent to the native heart valve (e.g., the aortic valve). Alternative approaches to treat a defective aortic valve and/or other heart valve(s) are also contemplated with the implant delivery system 30.

The desired insertion depth may be selected to maximize radially outward force of the expandable framework 12 within the native heart valve (e.g., the aortic valve). Positioning the replacement heart valve implant 10 at the desired insertion depth and/or within a maximum tolerance from the desired insertion depth, the replacement heart valve implant 10 and/or the expandable framework 12 may exhibit optimal arching within the native heart valve (e.g., the aortic valve) and thereby prevent migration of the replacement heart valve implant 10 and/or the expandable framework 12 downstream (or upstream).

Positioning the replacement heart valve implant 10 and/or the expandable framework 12 within the native heart valve (e.g., the aortic valve) may be accomplished by locating the primary visual indicator relative to the native heart valve (e.g., the aortic valve). During visualization, the native heart valve (e.g., the aortic valve) may be identified and/or visualized under fluoroscopy using known means and/or methods, such as contrast injection.

In some embodiments, the implant delivery system 30 and/or the elongate shaft assembly 50 may include the stent holder 70 configured to engage the expandable framework 12 of the replacement heart valve implant 10 in the radially collapsed configuration and/or when the replacement heart valve implant 10 is constrained within the implant holding portion 60 of the implant delivery system 30. In some embodiments, the stent holder 70 may include a body, a first end portion extending proximally from the body, and a second end portion disposed opposite the first end portion. In some embodiments, at least a portion of the first end portion may extend radially outward from and/or radially outward of the body. In some embodiments, the first end portion may have a generally bulbous shape. In some embodiments, the stent holder 70 may be configured and/or adapted to be visible under fluoroscopy. In some embodiments, the stent holder 70 may be formed from stainless steel. Some suitable but non-limiting materials for the stent holder 70 and/or components or elements thereof are described below.

In some embodiments, an outermost radial extent of the first end portion of the stent holder 70 may be disposed proximate a distal end of the first end portion of the stent holder 70. In some embodiments, the first end portion of the stent holder 70 may be tapered radially inward in a proximal direction from the outermost radial extent of the stent holder 70. In some embodiments, the stent holder 70 may include a lumen extending longitudinally and/or axially therethrough. In at least some embodiments, at least a portion of the elongate shaft assembly 50 may extend longitudinally and/or axially through the lumen of the stent holder 70.

The first end portion may be configured and/or adapted to engage the expandable framework 12 of the replacement heart valve implant 10 in the radially collapsed configuration and/or when the replacement heart valve implant 10 is constrained within the implant holding portion 60 of the implant delivery system 30. In some embodiments, the first end portion may include the at least one projection 73 configured and/or adapted to engage the expandable framework 12 of the replacement heart valve implant 10 in the radially collapsed configuration and/or when the replacement heart valve implant 10 is constrained within the implant holding portion 60 of the implant delivery system 30. In some embodiments, the at least one projection 73 may extend radially outward from the first end portion of the stent holder 70.

In some embodiments, the implant delivery system 30 and/or the implant holding portion 60 may include an atraumatic transition shield 79, seen in FIGS. 3-4. The atraumatic transition shield 79 may be disposed adjacent the stent holder 70. In some embodiments, the atraumatic transition shield 79 may be disposed between the stent holder 70 and the handle 40. In some embodiments, the atraumatic transition shield 79 may be disposed proximal of the stent holder 70. In some embodiments, the atraumatic transition shield 79 may be disposed at and/or adjacent the first end portion of the stent holder 70. In some embodiments, the atraumatic transition shield 79 may axially overlap the first end portion of the stent holder 70. In some embodiments, the atraumatic transition shield 79 may be disposed radially outward of at least a portion of the first end portion of the stent holder 70. In some embodiments, the atraumatic transition shield 79 may be tapered radially inward in the downstream direction and/or the proximal direction and/or toward the handle 40. The atraumatic transition shield 79 may be configured to prevent the replacement heart valve implant 10, the expandable framework 12, the plurality of valve leaflets 20, etc. from catching on the stent holder 70 as the implant delivery system 30 is withdrawn after deploying the replacement heart valve implant 10.

In some embodiments, the primary visual indicator may be disposed adjacent a proximal end of the atraumatic transition shield 79. In some embodiments, the primary visual indicator may be disposed downstream and/or proximal of the atraumatic transition shield 79. In some embodiments, the primary visual indicator and the atraumatic transition shield 79 may axially overlap. Other configurations are also contemplated.

In some embodiments, the elongate shaft assembly 50 may comprise an expandable balloon 80 disposed on the tubular member (e.g., the intermediate tubular member 56) within the implant holding portion 60. In some embodiments, the expandable balloon 80 may be secured to the tubular member (e.g., the intermediate tubular member 56). In some embodiments, the expandable balloon 80 may be fixedly attached to the tubular member (e.g., the intermediate tubular member 56). In some embodiments, the expandable balloon 80 may be configured to shift between a deflated configuration (e.g., FIGS. 2-3) and an inflated configuration (e.g., FIGS. 3-4). For reference, the inflated configuration of the expandable balloon 80 is shown in FIG. 3 in phantom.

As seen in FIG. 2, when the replacement heart valve implant 10 and/or the expandable framework 12 is constrained within the implant holding portion 60 in the radially collapsed configuration, at least a portion of the replacement heart valve implant 10 and/or the expandable framework 12 extends upstream and/or distal of the expandable balloon 80 in the deflated configuration. It is noted that relative positioning of at least a portion of the replacement heart valve implant 10 and/or the expandable framework 12 (e.g., the inflow end, the distal portion, the anchoring portion, etc.) does not substantially change with respect to the expandable balloon 80 when the replacement heart valve implant 10 and/or the expandable framework 12 shifts from the radially collapsed configuration shown in FIG. 2 to the radially expanded configuration shown in FIG. 3.

In at least some embodiments, the expandable balloon 80 may include a proximal tapered portion 82 (e.g., a downstream tapered portion), a distal tapered portion 84 (e.g., an upstream tapered portion), and a body portion 86 extending from the proximal tapered portion 82 (e.g., the downstream tapered portion) to the distal tapered portion 84 (e.g., the upstream tapered portion). In some embodiments, the body portion 86 may have a generally constant outer diameter and/or profile from the proximal tapered portion 82 (e.g., the downstream tapered portion) to the distal tapered portion 84 (e.g., the upstream tapered portion). In some embodiments, the expandable balloon 80 may be fixedly attached to the elongate shaft assembly 50, the tubular member, the intermediate tubular member 56, and/or elements thereof at a proximal waist 81 (e.g., a downstream waist) and at a distal waist 83 (e.g., an upstream waist). In some embodiments, the primary visual indicator may be disposed within and/or radially inward of the expandable balloon 80. In some embodiments, the primary visual indicator may be disposed within and/or radially inward of the body portion 86 of the expandable balloon 80. Other configurations are also contemplated.

As seen in FIG. 3 for example, the replacement heart valve implant 10 and/or the expandable framework 12 has a greater axial length than the body portion 86 of the expandable balloon 80. In some embodiments, the replacement heart valve implant 10 and/or the expandable framework 12 may have a first overall axial length and the expandable balloon 80 may have a second overall axial length, wherein the first overall axial length is greater than the second overall axial length. Other configurations are also contemplated.

In at least some embodiments, the expandable balloon 80 may be non-compliant and/or may be formed from a substantially non-compliant material. In some alternative embodiments, the expandable balloon 80 may by formed from a semi-compliant material, or a blend of compliant and non-compliant materials. In some further alternative embodiments, the expandable balloon 80 may be formed from a compliant material. Some suitable but non-limiting examples of materials for forming the expandable balloon 80, including polymeric and/or metallic materials, are discussed below.

In some embodiments, the expandable balloon 80 may have a fixed outer diameter in the inflated configuration. In at least some embodiments, the fixed outer diameter, the generally constant outer diameter, and/or the profile from the proximal tapered portion 82 (e.g., the downstream tapered portion) to the distal tapered portion 84 (e.g., the upstream tapered portion) to be within 10% of a desired inner diameter of the tubular wall of the expandable framework 12. In some embodiments, the fixed outer diameter, the generally constant outer diameter, and/or the profile from the proximal tapered portion 82 (e.g., the downstream tapered portion) to the distal tapered portion 84 (e.g., the upstream tapered portion) to be within 7.5% of a desired inner diameter of the tubular wall of the expandable framework 12. In some embodiments, the fixed outer diameter, the generally constant outer diameter, and/or the profile from the proximal tapered portion 82 (e.g., the downstream tapered portion) to the distal tapered portion 84 (e.g., the upstream tapered portion) to be within 5% of a desired inner diameter of the tubular wall of the expandable framework 12. In some embodiments, the fixed outer diameter, the generally constant outer diameter, and/or the profile from the proximal tapered portion 82 (e.g., the downstream tapered portion) to the distal tapered portion 84 (e.g., the upstream tapered portion) to be within 2.5% of a desired inner diameter of the tubular wall of the expandable framework 12. Other configurations are also contemplated.

In some embodiments, upon release of the replacement heart valve implant 10 and/or the expandable framework 12 from the implant holding portion 60, the replacement heart valve implant 10 and/or the expandable framework 12 is configured to shift toward the radially expanded configuration and the inflow end and/or the lower crown 14 is offset longitudinally and/or axially from the body portion 86 of the expandable balloon 80 in the deflated configuration and before shifting to the inflated configuration, as seen in FIG. 3. In some embodiments, the inflow end and/or the lower crown 14 is offset distally and/or in an upstream direction from the body portion 86 of the expandable balloon 80 in the deflated configuration and before shifting to the inflated configuration. In some embodiments, the plurality of stabilization arches 18 may extend proximal and/or downstream of the body portion 86 of the expandable balloon 80 when the inflow end and/or the lower crown 14 is offset distally and/or in an upstream direction from the body portion 86 of the expandable balloon 80 in the deflated configuration and before shifting to the inflated configuration.

In some embodiments, the implant delivery system 30 may be configured to advance the expandable balloon 80, the tubular member (e.g., the intermediate tubular member 56), the implant holding portion 60, and/or the implant delivery system 30 itself distally and/or upstream relative to the replacement heart valve implant 10 and/or the expandable framework 12 before shifting the expandable balloon 80 toward and/or to the inflated configuration. In some embodiments, the implant delivery system 30 may be configured to center the body portion 86 of the expandable balloon 80 with respect to and/or relative to the inflow end and the outflow end of the replacement heart valve implant 10 and/or the expandable framework 12 before shifting the expandable balloon 80 from the deflated configuration toward and/or to the inflated configuration.

In some procedures, after releasing the replacement heart valve implant 10 and/or the expandable framework 12 from the implant holding portion 60 and/or after the replacement heart valve implant 10 and/or the expandable framework 12 has shifted toward the radially expanded configuration, the replacement heart valve implant 10 and/or the expandable framework 12 may be incompletely seated within the native heart valve (e.g., the aortic valve) and/or paravalvular leakage may occur around the replacement heart valve implant 10 and/or the expandable framework 12 due to variations in anatomy, calcification of the native heart valve (e.g. the aortic valve), etc. In some procedures, it may be beneficial to apply additional radially outward force to the replacement heart valve implant 10 and/or the expandable framework 12 after deployment in order to better seat the replacement heart valve implant 10 and/or the expandable framework 12 within the native valve (e.g., the aortic valve). In some embodiments, application of additional radially outward force to the replacement heart valve implant 10 and/or the expandable framework 12 after deployment and/or after shifting toward the radially expanded configuration may be optional.

In some embodiments, the implant delivery system 30 may be configured to inflate the expandable balloon 80 within the replacement heart valve implant 10 and/or the expandable framework 12 to urge a portion of the replacement heart valve implant 10 and/or the expandable framework 12 radially outward against the native heart valve (e.g., the aortic valve), as seen in FIG. 4. In some embodiments, the expandable balloon 80 may be configured to urge the anchoring portion, the tubular wall, etc. of the replacement heart valve implant 10 and/or the expandable framework 12 radially outward when the expandable balloon 80 is shifted from the deflated configuration to the inflated configuration. In some embodiments, the body portion 86 of the expandable balloon 80 may be configured to urge the anchoring portion, the tubular wall, etc. of the replacement heart valve implant 10 and/or the expandable framework 12 radially outward when the expandable balloon 80 is shifted from the deflated configuration to the inflated configuration.

As seen in FIG. 4, the implant delivery system 30 may include the inflation port 46 disposed on and/or within the handle 40. The implant delivery system 30 and/or the tubular member (e.g., the intermediate tubular member 56) may include an inflation lumen 48 extending from the handle 40 and/or the inflation port 46 on the handle 40 to the expandable balloon 80. The inflation lumen 48 may be in fluid communication with the expandable balloon 80 and the inflation port 46. The inflation lumen 48 may be configured to carry and/or transfer inflation fluid (e.g., saline, etc.) between an inflation fluid source coupled to the inflation port 46 and the expandable balloon 80.

Figure 5:
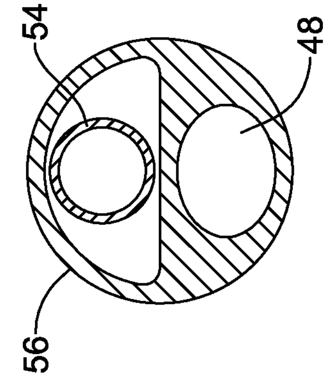

In some embodiments, the tubular member (e.g., the intermediate tubular member 56) may include a plurality of lumens formed and/or extending therein, wherein the plurality of lumens includes the inflation lumen 48, as seen in the partial cross-sectional view of FIG. 5. For clarity, structures outside of the tubular member (e.g., the intermediate tubular member 56) have been omitted from FIG. 5. The inner shaft 54 may be disposed within and/or may extend within one lumen of the plurality of lumens. In at least some embodiments, the inner shaft 54 may be disposed within and/or may extend within a lumen different from the inflation lumen 48. Other configurations are also contemplated.

Figure 6:
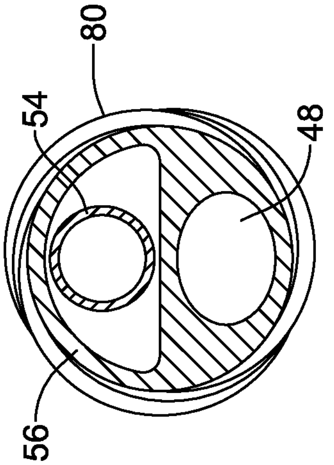
FIGS. 5-8 are partial cross-sectional views illustrating selected aspects of the replacement heart valve system.
Figure 8:
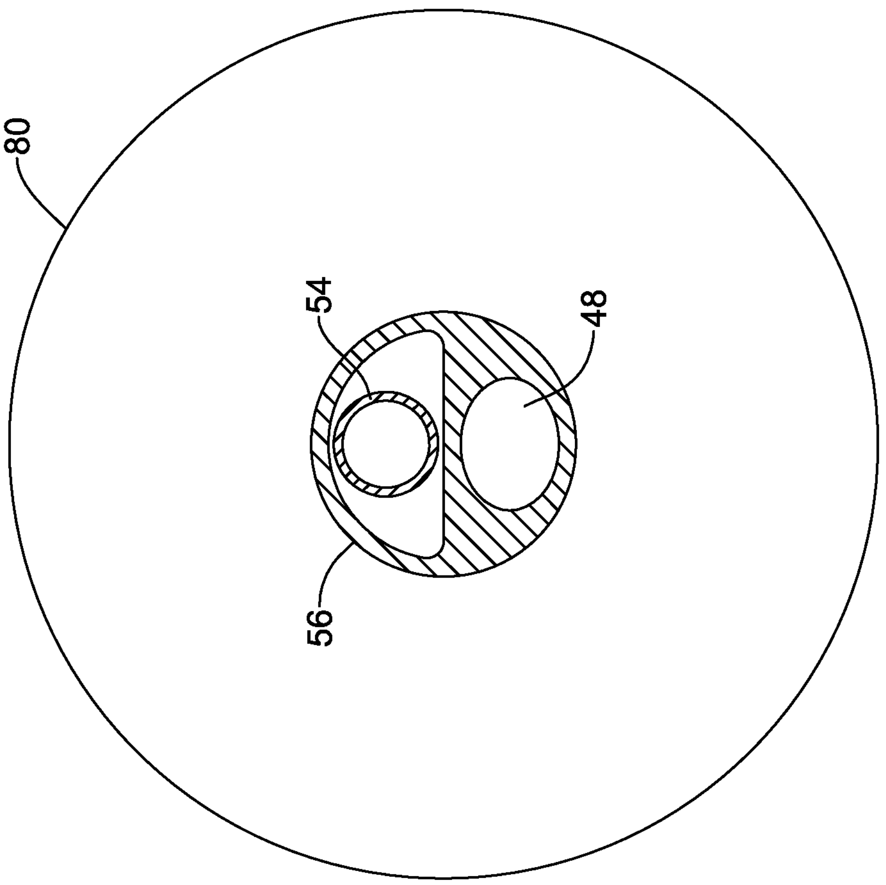
Figure 7:
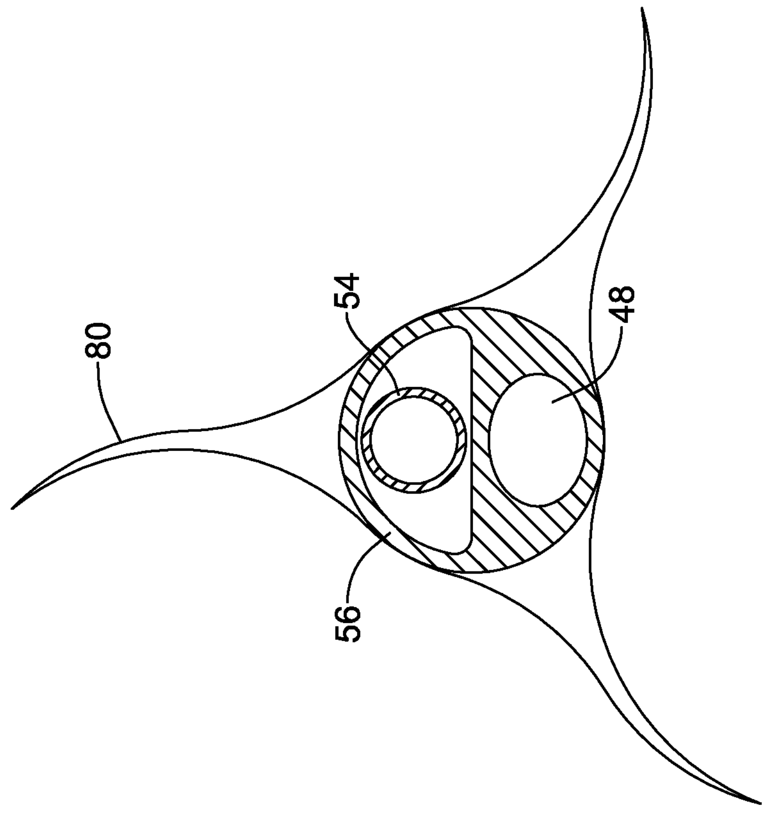

FIGS. 6-8 are partial cross-sectional views illustrating selected aspects related to the expandable balloon 80. Some features have been omitted in the interest of clarity. As seen in FIG. 6, when the expandable balloon 80 is in the deflated configuration, the expandable balloon 80 may be wrapped around the tubular member (e.g., the intermediate tubular member 56). In at least some embodiments, the expandable balloon 80 may be self-biased toward the deflated configuration. In some embodiments, the expandable balloon 80 may be heat set in the deflated configuration. As such, when inflation fluid in removed from the expandable balloon 80, the expandable balloon 80 may be configured to wrap itself around the tubular member (e.g., the intermediate tubular member 56). FIG. 7 is a partial cross-sectional view of the expandable balloon 80 in a partially inflated configuration (e.g., between the deflated configuration and the inflated configuration). As seen in FIG. 7, the expandable balloon 80 may be self-biased toward the deflated configuration and may be configured to assume the deflated configuration when unbiased radially outward by inflation fluid disposed within the expandable balloon 80. FIG. 8 is a partial cross-sectional view of the expandable balloon 80 in the inflated configuration. In the inflated configuration and/or when the expandable balloon 80 is filled with inflation fluid, the expandable balloon 80 may be biased radially outward toward and/or to the inflated configuration by the inflation fluid.

A method of delivering the replacement heart valve implant 10 to a native heart valve (e.g., the aortic valve) may comprise advancing the implant delivery system 30 to a position adjacent the native heart valve (e.g., the aortic valve). As discussed herein, the replacement heart valve implant 10 and/or the expandable framework 12 may be constrained within the implant holding portion 60 of the implant delivery system 30 in a radially collapsed configuration, as seen in FIG. 2. The method of delivering the replacement heart valve implant 10 to the native heart valve (e.g., the aortic valve) may further comprise releasing and/or deploying the replacement heart valve implant 10 and/or the expandable framework 12 from the implant holding portion 60 of the implant delivery system 30 within the native heart valve (e.g., the aortic valve) such that the replacement heart valve implant 10 and/or the expandable framework 12 is permitted to shift from the radially collapsed configuration toward and/or to the radially expanded configuration.

As discussed herein, the implant delivery system 30 may comprise the expandable balloon 80 disposed on the tubular member (e.g., the intermediate tubular member 56) within the implant holding portion 60. The expandable balloon 80 may be configured to shift between the deflated configuration and the inflated configuration. In at least some embodiments, when the replacement heart valve implant 10 and/or the expandable framework 12 is constrained within the implant holding portion 60 in the radially collapsed configuration, at least a portion of the replacement heart valve implant 10 and/or the expandable framework 12 extends upstream and/or distal of the expandable balloon 80 in the deflated configuration. In some embodiments, when the replacement heart valve implant 10 and/or the expandable framework 12 is constrained within the implant holding portion 60 in the radially collapsed configuration, at least a portion of the replacement heart valve implant 10 and/or the expandable framework 12 extends downstream and/or proximal of the expandable balloon 80 in the deflated configuration.

In some embodiments, releasing and/or deploying the replacement heart valve implant 10 and/or the expandable framework 12 within the native heart valve (e.g., the aortic valve) may further comprise shifting the proximal sheath 62 of the implant delivery system 30 and/or the implant holding portion 60 downstream and/or proximally relative to the replacement heart valve implant 10 and/or the expandable framework 12 to release the proximal portion of the replacement heart valve implant 10 and/or the expandable framework 12, thereby permitting the proximal portion of the replacement heart valve implant 10 and/or the expandable framework 12 to shift toward the radially expanded configuration. In some embodiments, deploying the replacement heart valve implant 10 and/or the expandable framework 12 within the native heart valve (e.g., the aortic valve) may further comprise thereafter, shifting the distal sheath 64 of the implant delivery system 30 and/or the implant holding portion 60 upstream and/or distally relative to the replacement heart valve implant 10 and/or the expandable framework 12 to release the distal portion of the replacement heart valve implant 10 and/or the expandable framework 12, thereby permitting the distal portion of the replacement heart valve implant 10 and/or the expandable framework 12 to shift toward the radially expanded configuration, as seen in FIG. 3.

In some embodiments, after releasing and/or deploying the replacement heart valve implant 10 and/or the expandable framework 12 within the native heart valve (e.g., the aortic valve), the method may comprise shifting the implant holding portion 60 from the open configuration to the closed configuration. For example, shifting the implant holding portion 60 from the open configuration to the closed configuration may include moving and/or translating the proximal sheath 62 and the distal sheath 64 towards each other. In some embodiments, shifting the implant holding portion 60 from the open configuration to the closed configuration may include moving and/or translating the proximal sheath 62 upstream and/or distally relative to the tubular member (e.g., the intermediate tubular member 56) and/or moving and/or translating the distal sheath 64 downstream and/or proximally relative to the tubular member (e.g., the intermediate tubular member 56).

In some embodiments, after releasing and/or deploying the replacement heart valve implant 10 and/or the expandable framework 12 within the native heart valve (e.g., the aortic valve), the method may comprise retraction and/or withdrawal of the implant delivery system 30 relative to the replacement heart valve implant 10 and/or the expandable framework 12. In some embodiments, after deploying the replacement heart valve implant 10 and/or the expandable framework 12 within the native heart valve (e.g., the aortic valve), the method may comprise retraction and/or withdrawal of the implant delivery system 30 from the treatment site, from the position adjacent the native heart valve (e.g., the aortic valve), and/or from the patient.

In at least some interventions, the replacement heart valve implant 10 may be deployed within the native heart valve (e.g., the native heart valve is left in place and not excised). Alternatively, the native heart valve may be removed (such as through valvuloplasty, for example) and the replacement heart valve implant 10 may be deployed in its place as a replacement.

In some embodiments, the method of delivering the replacement heart valve implant 10 to a native heart valve (e.g., the aortic valve) may further comprise translating the implant delivery system 30 relative to the replacement heart valve implant 10 and/or the expandable framework 12 to position the expandable balloon 80 within the replacement heart valve implant 10 and/or the expandable framework 12 such that at least a portion of the expandable balloon 80 extends upstream and/or distal of the replacement heart valve implant 10 and/or the expandable framework 12, and shifting the expandable balloon 80 toward and/or to the inflated configuration within the replacement heart valve implant 10 and/or the expandable framework 12 to urge a portion (e.g., the anchoring portion, the tubular wall, etc.) of the replacement heart valve implant 10 and/or the expandable framework 12 radially outward.

Urging the portion (e.g., the anchoring portion, the tubular wall, etc.) of the replacement heart valve implant 10 and/or the expandable framework 12 radially outward with the expandable balloon 80 may improve engagement of the replacement heart valve implant 10 and/or the expandable framework 12 radially outward with the native heart valve (e.g., the aortic valve) and/or reduce paravalvular leakage. In some embodiments, some obstruction or anomaly may prevent full and/or complete expansion and/or shift of the replacement heart valve implant 10 and/or the expandable framework 12 to the radially expanded configuration. The expandable balloon 80 on the implant delivery system 30 may permit the user to further shift and/or urge the replacement heart valve implant 10 and/or the expandable framework 12 toward and/or to the radially expanded configuration without needing to exchange a catheter and/or introduce another device into the patient, thereby saving time, preventing patient injury due to translation of the device(s), and/or reducing overall risk to the patient.

In some embodiments, translating the implant delivery system 30 relative to the replacement heart valve implant 10 and/or the expandable framework 12 may include translating the expandable balloon 80 upstream and/or distally relative to the replacement heart valve implant 10 and/or the expandable framework 12 to longitudinally center the body portion 86 of the expandable balloon 80 with respect to and/or relative to the inflow end (e.g., the lower crown 14) and the outflow end (e.g., the upper crown 16) under fluoroscopy prior to shifting the expandable balloon 80 toward and/or to the inflated configuration.

In some embodiments, the implant delivery system 30 may include at least one radiopaque marker 90 correlated to the expandable balloon 80 and configured to center the body portion 86 of the expandable balloon 80 with respect to and/or relative to the inflow end (e.g., the lower crown 14) and the outflow end (e.g., the upper crown 16) under fluoroscopy prior to shifting the expandable balloon 80 toward and/or to the inflated configuration. In some embodiments, the at least one radiopaque marker 90 may be disposed at, on, and/or in the proximal waist 81, the distal waist 83, and/or along the tubular member (e.g., the intermediate tubular member 56) between the proximal waist 81 and the distal waist 83, as shown in FIG. 3. Other configurations and/or locations for the at least one radiopaque marker 90 are also contemplated.

In some embodiments, the method of delivering the replacement heart valve implant 10 to a native heart valve (e.g., the aortic valve) may further comprise, after releasing and/or deploying the replacement heart valve implant 10 and/or the expandable framework 12 within the native heart valve (e.g., the aortic valve), assessing deployment of the replacement heart valve implant 10 and/or the expandable framework 12 within the native heart valve (e.g., the aortic valve) for paravalvular leakage prior to withdrawing the implant delivery system 30 from the position adjacent the native heart valve (e.g., the aortic valve), and/or from the patient.

In some embodiments, if paravalvular leakage exceeds a predetermined value, the method of delivering the replacement heart valve implant 10 to a native heart valve (e.g., the aortic valve) may further comprise translating the implant delivery system 30 relative to the replacement heart valve implant 10 and/or the expandable framework 12 to position the expandable balloon 80 within the replacement heart valve implant 10 and/or the expandable framework 12 such that at least a portion of the expandable balloon 80 extends upstream and/or distal of the replacement heart valve implant 10 and/or the expandable framework 12, and shifting the expandable balloon 80 toward and/or to the inflated configuration within the replacement heart valve implant 10 and/or the expandable framework 12 to urge a portion (e.g., the anchoring portion, the tubular wall, etc.) of the replacement heart valve implant 10 and/or the expandable framework 12 radially outward.

Urging the portion (e.g., the anchoring portion, the tubular wall, etc.) of the replacement heart valve implant 10 and/or the expandable framework 12 radially outward with the expandable balloon 80 may improve engagement of the replacement heart valve implant 10 and/or the expandable framework 12 radially outward with the native heart valve (e.g., the aortic valve) and/or reduce paravalvular leakage. In some embodiments, some obstruction or anomaly may prevent full and/or complete expansion and/or shift of the replacement heart valve implant 10 and/or the expandable framework 12 to the radially expanded configuration. The expandable balloon 80 on the implant delivery system 30 may permit the user to further shift and/or urge the replacement heart valve implant 10 and/or the expandable framework 12 toward and/or to the radially expanded configuration without needing to exchange a catheter and/or introduce another device into the patient, thereby saving time, preventing patient injury due to translation of the device(s), and/or reducing overall risk to the patient.

In some embodiments, if paravalvular leakage does not exceed the predetermined value, the method of delivering the replacement heart valve implant 10 to a native heart valve (e.g., the aortic valve) may further comprise retraction and/or withdrawal of the implant delivery system 30 from the treatment site, from the position adjacent the native heart valve (e.g., the aortic valve), and/or from the patient. In some alternative embodiments, even if paravalvular leakage does not exceed the predetermined value, the method of delivering the replacement heart valve implant 10 to a native heart valve (e.g., the aortic valve) may further comprise translating the implant delivery system 30 relative to the replacement heart valve implant 10 and/or the expandable framework 12 to position the expandable balloon 80 within the replacement heart valve implant 10 and/or the expandable framework 12 such that at least a portion of the expandable balloon 80 extends upstream and/or distal of the replacement heart valve implant 10 and/or the expandable framework 12, and shifting the expandable balloon 80 toward and/or to the inflated configuration within the replacement heart valve implant 10 and/or the expandable framework 12 to urge a portion (e.g., the anchoring portion, the tubular wall, etc.) of the replacement heart valve implant 10 and/or the expandable framework 12 radially outward.

Urging the portion (e.g., the anchoring portion, the tubular wall, etc.) of the replacement heart valve implant 10 and/or the expandable framework 12 radially outward with the expandable balloon 80 may improve engagement of the replacement heart valve implant 10 and/or the expandable framework 12 radially outward with the native heart valve (e.g., the aortic valve) and/or reduce paravalvular leakage. In some embodiments, some obstruction or anomaly may prevent full and/or complete expansion and/or shift of the replacement heart valve implant 10 and/or the expandable framework 12 to the radially expanded configuration. The expandable balloon 80 on the implant delivery system 30 may permit the user to further shift and/or urge the replacement heart valve implant 10 and/or the expandable framework 12 toward and/or to the radially expanded configuration without needing to exchange a catheter and/or introduce another device into the patient, thereby saving time, preventing patient injury due to translation of the device(s), and/or reducing overall risk to the patient.

The materials that can be used for the various components of the replacement heart valve system and the various elements thereof disclosed herein may include those commonly associated with medical devices. For simplicity purposes, the following discussion refers to the system. However, this is not intended to limit the devices, components, and methods described herein, as the discussion may be applied to other elements, members, components, or devices disclosed herein, such as, but not limited to, the replacement heart valve implant, the expandable framework, the plurality of valve leaflets, the implant delivery system, the handle, the elongate shaft assembly, the expandable balloon, etc. and/or elements or components thereof.

In some embodiments, the system and/or components thereof may be made from a metal, metal alloy, polymer, a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM; for example, DELRIN®), polyether block ester, polyurethane, polypropylene (PP), polyvinylchloride (PVC), polyether-ester (for example, ARNITEL®), ether or ester based copolymers (for example, butylene/poly(alkylene ether) phthalate and/or other polyester elastomers such as HYTREL®), polyamide (for example, DURETHAN® or CRISTAMID®), elastomeric polyamides, block polyamide/ethers, polyether block amide (PEBA; for example, PEBAX®), ethylene vinyl acetate copolymers (EVA), silicones, polyethylene (PE), MARLEX® high-density polyethylene, MARLEX® low-density polyethylene, linear low density polyethylene (for example, REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID®), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, Elast-Eon® or ChronoSil®), biocompatible polymers, other suitable materials, or mixtures, combinations, copolymers thereof, polymer/metal composites, and the like. In some embodiments, the system and/or components thereof can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In at least some embodiments, portions or all of the system and/or components thereof may also be doped with, made of, or otherwise include a radiopaque material. Radiopaque materials are understood to be materials capable of producing a relatively bright image on a fluoroscopy screen or another imaging technique (e.g., ultrasound, etc.) during a medical procedure. This relatively bright image aids the user of the system in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the system to achieve the same result.

In some embodiments, a degree of Magnetic Resonance Imaging (MRI) compatibility is imparted into the system and/or other elements disclosed herein. For example, the system and/or components or portions thereof may be made of a material that does not substantially distort the image and create substantial artifacts (e.g., gaps in the image). Certain ferromagnetic materials, for example, may not be suitable because they may create artifacts in an MRI image. The system or portions thereof may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-NR and the like), nitinol, and the like, and others.

In some embodiments, the system and/or other elements disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the system and/or other elements disclosed herein may include and/or be formed from a textile material. Some examples of suitable textile materials may include synthetic yarns that may be flat, shaped, twisted, textured, pre-shrunk or un-shrunk. Synthetic biocompatible yarns suitable for use in the present disclosure include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum, or a Ni—Co—Cr-based alloy. The yarns may further include carbon, glass, or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun types. The type and denier of the yarn chosen may be selected in a manner which forms a biocompatible and implantable prosthesis and, more particularly, a vascular structure having desirable properties.

In some embodiments, the system and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethyl ketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); immunosuppressants (such as the "olimus" family of drugs, rapamycin analogues, macrolide antibiotics, biolimus, everolimus, zotarolimus, temsirolimus, picrolimus, novolimus, myolimus, tacrolimus, sirolimus, pimecrolimus, etc.); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The scope of the disclosure is, of course, defined in the language in which the appended claims are expressed.

What is claimed is:

1. A replacement heart valve system comprising:

a replacement heart valve implant comprising:

an expandable framework configured to shift from a radially collapsed configuration to a radially expanded configuration, wherein the expandable framework is self-biased toward the radially expanded configuration and the expandable framework includes an anchoring portion extending from an inflow end to an outflow end, and a plurality of stabilization arches extending downstream from the outflow end; and a plurality of valve leaflets attached to the expandable framework; and an implant delivery system comprising a handle and an elongate shaft assembly, the elongate shaft assembly comprising a tubular member fixedly attached to the handle, and a distally-positioned implant holding portion configured to constrain the expandable framework in the radially collapsed configuration;

wherein the elongate shaft assembly further comprises an expandable balloon disposed on the tubular member within the implant holding portion and positioned within the constrained expandable framework, the expandable balloon including a proximal tapered portion, a distal tapered portion, and a body portion extending from the proximal tapered portion to the distal tapered portion, and wherein the expandable balloon is configured to shift between a deflated configuration and an inflated configuration;

wherein upon release from the implant holding portion, the expandable framework is configured to shift toward the radially expanded configuration and the inflow end is offset distally from the distal tapered portion of the expandable balloon in the deflated configuration and before shifting to the inflated configuration.

2. The replacement heart valve system of claim 1, wherein the plurality of stabilization arches extends proximal of the body portion of the expandable balloon when the inflow end is offset distally from the distal tapered portion of the expandable balloon in the deflated configuration.

3. The replacement heart valve system of claim 1, wherein the implant delivery system is configured to advance the expandable balloon distally relative to the expandable framework before shifting the expandable balloon from the deflated configuration to the inflated configuration.

4. The replacement heart valve system of claim 3, wherein the implant delivery system is configured to center the body portion of the expandable balloon longitudinally within the expandable framework with respect to the inflow end and the outflow end before shifting the expandable balloon from the deflated configuration to the inflated configuration.

5. The replacement heart valve system of claim 4, wherein the body portion of the expandable balloon is configured to urge the anchoring portion of the expandable framework radially outward when the expandable balloon is shifted from the deflated configuration to the inflated configuration.

* * * * *